(12) United States Patent
Rahme et al.

(10) Patent No.: US 8,906,602 B2
(45) Date of Patent: Dec. 9, 2014

(54) METHODS FOR IDENTIFYING CANDIDATE COMPOUNDS FOR TREATING, REDUCING, OR PREVENTING PATHOGENIC INFECTIONS

(75) Inventors: Laurence Rahme, Jamaica Plain, MA (US); Eric Deziel, Mascouche (CA); Francois Lepine, Longueuil (CA); Ronald G. Tompkins, Boston, MA (US); Gaoping Xiao, New Haven, CT (US)

(73) Assignee: The General Hospital Corporation, Boston, MA (US)

( * ) Notice: Subject to any disclaimer, the term of this patent is extended or adjusted under 35 U.S.C. 154(b) by 1890 days.

(21) Appl. No.: 10/586,403

(22) PCT Filed: Jan. 21, 2005

(86) PCT No.: PCT/US2005/002174
§ 371 (c)(1),
(2), (4) Date: May 24, 2007

(87) PCT Pub. No.: WO2005/069989
PCT Pub. Date: Aug. 4, 2005

(65) Prior Publication Data
US 2007/0292851 A1    Dec. 20, 2007

Related U.S. Application Data

(60) Provisional application No. 60/538,278, filed on Jan. 21, 2004, provisional application No. 60/538,361, filed on Jan. 22, 2004.

(51) Int. Cl.
*C12Q 1/00* (2006.01)
*A61K 39/108* (2006.01)
*A01N 63/00* (2006.01)
*C12Q 1/18* (2006.01)

(52) U.S. Cl.
CPC .............. *C12Q 1/18* (2013.01); *G01N 2333/21* (2013.01)
USPC ... 435/4; 435/29; 435/32; 435/41; 424/234.1; 424/260.1; 424/93.1; 424/93.4

(58) Field of Classification Search
None
See application file for complete search history.

(56) References Cited

PUBLICATIONS

Déziel et al., "Analysis of *Pseudomonas aeruginosa* 4-hydroxy-2-alkylquinolines (HAQs) reveals a role for 4-hydroxy-2-heptylquinoline in cell-to-cell communication," Proc. Natl. Acad. Sci. U.S.A. 101:1339-1344 (2004).
International Preliminary Report on Patentability, PCT/US05/02174, issued Jul. 31, 2006.
International Search Report, PCT/US05/02174, mailed Jul. 7, 2006.

*Primary Examiner* — Rodney P Swartz
(74) *Attorney, Agent, or Firm* — Clark & Elbing LLP

(57) ABSTRACT

Disclosed are methods for identifying candidate compounds for treating, reducing, or preventing a pathogenic infection, the methods including: (a) contacting a pathogenic cell with a candidate compound; and (b) measuring the production of a molecule selected from the group consisting of an 4-hydroxy-2-alkylquinoline (HAQ) molecule, 4-hydroxy-2-heptylquinoline (HHQ) molecule, or a derivative or precursor thereof in the cell, a candidate compound that reduces the production relative to production of the molecule by a cell not contacted with the candidate compound, identifying a candidate compound useful for treating, reducing, or preventing a pathogenic infection.

9 Claims, 20 Drawing Sheets pqsA (SEQ ID NO:1)
ATGTCCACATTGGCCAACCTGACCGAGGTTCTGTTCCGCCTCGATTTCGATCCCGATACCGCCGTTTATCA
CTATCGGGGCCAGACTCTCAGCCGGCTGCAATGCCGGACCTACATTCTCTCCCAGGCCAGCCAACTGGCCC
GCCTGCTCAAGCCCGGCGATCGCGTGGTGCTGGCGTTGAACGACTCGCCTTCGCTGGCCTGCCTGTTCCTG
GCCTGCATCGCGGTCGGCGCCATTCCCGCCGTGATCAATCCCAAGTCCCGCGAGCAGGCCCTGGCCGATAT
CGCTGCCGACTGCCAGGCCAGCCTGGTGGTGCGTGAAGCCGATGCACCGTCGCTGAGCGGTCCTTTGGCGC
CGTTGACCCTGCGTGCGGCCGCCGGACGCCCTTTGCTCGACGATTTCTCGCTGGACGCGCTGGTCGGCCCT
GCGGACCTCGATTGGAGTGCCTTCCATCGCCAGGACCCGGCGGCAGCCTGTTCCTGCAATACACCTCGGG
TTCCACCGGGGCGCCCAAGGGGGTGATGCACAGCCTGCGCAACACGCTCGGTTTCTGCCGGGCGTTCGCTA
CGGAGTTGCTGGCATTGCAGGCGGGAGACCGGCTGTATTCGATTCCCAAGATGTTCTTCGGCTATGGCATG
GGCAACAGCCTGTTCTTTCCCTGGTTCAGCGGAGCCTCGGCGCTGCTCGACGATACCTGGCCGAGCCCGGA
GCGGGTTCTGGAGAACCTGGTCGCCTTCCGCCCCGGGTCCTGTTTGGGGTGCCGGCCATCTATGCCTCGC
TGCGTCCGCAGGCCAGGGAGCTGTTGAGCAGCGTGCGCCTGGCGTTTTCCGCCGGCTCGCCGCTGCCGCGC
GGCGAGTTCGAATTCTGGGCCGCGCACGGGCTGGAGATCTGCGACGGCATCGGGGCTACCGAGGTCGGCCA
TGTGTTCCTCGCCAACCGCCCGGGCCAGGCGCGTGCCGACAGCACCGGGCTGCCGTTGCCTGGCTATGAGT
GCCGGCTGGTGGACCGCGAAGGACACACTATCGAGGAAGCGGGCCGGCAAGGCGTGCTGTTGGTGCGTGGC
CCAGGGCTGAGTCCGGGTTACTGGCGGGCCAGCGAAGAGCAGCAGGCGCGCTTCGCAGGTGGCTGGTACCG
CACCGGCGACCTGTTCGAGCGCGACGAGTCGGGTGCCTACCGTCACTGTGGGCGGGAAGACGATCTGTTCA
AGGTGAATGGCCGCTGGGTGGTGCCGACCCAGGTCGAGCAGGCGATCTGCCGTCATCTGCCGGAAGTGAGC
GAGGCGGTTCTGGTTCCTACCTGCCGGCTGCACGACGGCTTGCGTCCGACCCTGTTCGTCACCCTGGCCAC
TCCGCTGGACGACAACCAGATCCTGCTGGCGCAGCGCATCGACCAGCATCTCGCCGAACAGATTCCCTCGC
ACATGCTGCCCAGCCAATTGCATGTGCTGCCGGCCTTGCCGCGCAACGACAACGGCAAGTTGGCGCGCGCC
GAGCTGCGCCACCTGGCCGACACCCTTTATCACGACAACCTTCCGGAGGAACGGGCATGTTGA pqsB (SEQ ID NO:2)
ATGTTGATTCAGGCTGTGGGGGTGAACCTGCCCCCATCCTATGTGTGTCTGGAGGGGCCGCTGGGAGGCGA
ACGCCCTCGCGCCCAGGGCGACGAGATGCTGATGCAGCGCTTGCTGCCGGCGGTTCGCGAAGCCCTGGACG
AGGCGGCGGTCAAGCCCGAGGAGATCGACCTGATCGTCGGCCTCGCCCTGTCTCCCGACCATCTGATCGAG
AACCGCGACATCATGGCGCCGAAGATCGGCCATCCGTTGCAGAAGGTCCTCGGCGCGAATCGCGCGCATGT
CTTCGACCTCACCGACTCGAGCCTGGCCCGCGCCCTCTACGTGGTCGATACCCTCGCCAGCGACCAGGGCT
ATCGCAACGTCCTGGTCGTGCGCGGCGAATCCAGCCAGGGATTGGAAGTGGACAGCGAGTCCGGCTTCGCC
CTTGCCGACGGCGCCCTGGCGCTGCTCTGCCGGCCGACCGGCAAGGCCGCGTTCCGTCGCGGTGCGCTGGG
CGGTGATCCGGCGCAGGAATGGCTGCCGCTGAGCATTCCGCTGAATACCGATATTCGCCAGGTAGGCGACG
TCAAGGGACACCTCAACCTGCCGGCCCAACCTGGATTGCCCGAAGCGGTACGCGCCGGATTCACCCGTCTG
GCCGGGGACTTCCCGCAACTGAACTGGGTGCGCGAGGAATGGTTCGGCCAGGGACGGCCCGATGGTCGTTG
CCTGGGGCCGTTCGAACTGGCGTCGCAACTGCGCGCGGCACAGCGCGACCGTCTGGATGAACTGCTGCTGA
TCAGCTTCGATCCGTTCGGCATGGTGGTGGAGGGCGTGACCCTGGAACTGGCGGGAGAAGCTCATGCATAA pqsC (SEQ ID NO:3)
ATGCATAAGGTCAAACTGGCAGCGATCACCTGTGAACTTCCGGCTCGCAGCTACGAAAACGACGATCCGGT
GTTCGCTGCGGTACCGGACCTCAGCGAGTCCTGGTGGCAATTCTGGGGCGTCAATCGGCGGGGCTATTTCG
ACCCGCGGAACGGCGAGAACGAGTTCAGCCTGGTGGTCCGGGCCGCCGAGCGCCTGCTGCGTAGCAGCGAT
ACCGCGCCGGATAGCGTGGACATGCTGATCTGTTCGGCTTCCTCGCCGATCATGACCGACGCCGGCGATGT
CCTGCCGGACCTGCGCGGACGTCTCTACCCGCGCATGGCCAACGTGCTGTCCAAGCAGCTCGGCCTGAGTC
GGGCGCTGCCATTGGATTCGCAGATGGAGTGCGCCAGCTTCCTGCTCAACCTGCGCCTGGCAGCGAGCATG
ATCCGCCAGGGTAAGGCCGAGAAAGTGCTGGTGGTGTGCAGCGAGTACATCTCCAACCTGCTCGACTTCAC
CTCGCGTACCTCGACCCTGTTCGCCGATGGCTGCGCGGTGGCCCTGCTGACCCGCGGCGACGATGACAGCT
GCGACCTGCTGGCTTCGGCCGAACACAGCGACGCTACGTTCTATGAAGTGGCCACCGGTCGCTGGCGCCTG
CCGGAAAACCCGACCGGCGAGGCCAAGCCGCGGCTTTATTTCTCGTTGTTCAGCGACGGCCAGAACAAGAT

Figure 11A

```
GGCCAGCTTCGTTCCGACCAACGTGCCGATCGCGATGCGCCGGGCGTTGGAAAAGGCCGGCCTGGGCAGCG
ATGACATCGATTATTTCGTCTTCCACCAGCCAGCGCCGTTCCTGGTCAAGGCCTGGGCCGAGGGCATCGGT
GCCCGTCCTGAGCAGTACCAACTGACGATGGGCGATACCGGCGTGATGATCTCCGTTTCCATCCCGTACAC
CCTGATGACCGGCCTGCGCGAGGGCAAGATCCGCCCCGGCGATCGTATCGTCATGGCCGGCGCAGCCACTG
GCTGGGGGTTCGCCGCCCAGGTCTGGCAATTGGGTGAGGTGCTGGTGTGCTGA
```

*pqsD* (SEQ ID NO:4)
```
ATGGGTAATCCGATCCTGGCCGGGCTGGGTTTCAGCCTGCCGAAACGCCAGGTCAGCAATCATGACCTGGT
AGGGCGCATCAATACGTCGGACGAGTTCATCGTCGAACGTACCGGCGTGCGCACCCGCTATACGTCGAGC
CGGAACAGGCGGTCAGCGCGCTGATGGTGCCGGCGGCGCGCCAGGCCATCGAGGCTGCCGGGCTGCTGCCG
GAGGACATCGACCTGTTGCTGGTGAACACCCTGTCGCCGGACCACCACGACCCGTCCCAGGCCTGCCTGAT
CCAGCCGCTGCTGGGCCTGCGGCACATCCCGGTACTGGATATCCGGGCACAGTGCAGCGGGTTGCTGTACG
GCTTGCAGATGGCTCGCGGGCAGATCCTCGCCGGGCTGGCACGGCATGTCCTGGTGGTCTGCGGCGAGGTG
CTGTCCAAGCGCATGGACTGTTCGGACCGCGGCCGCAACCTGTCGATCCTGCTCGGCGACGGTGCCGGCGC
AGTGGTGGTCAGCGCCGGCGAGAGTCTCGAAGACGGACTGCTGGACCTGCGCCTGGGCGCCGACGGCAACT
ACTTCGACCTGCTGATGACCGCGGCGCCGGGTAGTGCCTCGCCGACCTTCCTCGACGAGAATGTCCTGCGC
GAGGGCGGGGGCGAGTTCCTCATGCGCGGCCGGCCGATGTTCGAGCATGCCAGCCAGACCCTGGTACGGAT
CGCCGGCGAAATGCTCGCGGCCCATGAGCTGACCCTGGACGACATCGACCATGTGATCTGCCATCAACCGA
ACCTGCGCATCCTCGATGCGGTGCAGGAGCAACTGGGCATTCCCCAGCACAAGTTCGCGGTGACCGTGGAT
CGTCTGGGCAACATGGCTTCGGCCTCGACCCCGGTCACGCTGGCGATGTTCTGGCCGGACATCCAGCCGGG
ACAGCGGGTGCTGGTCCTGACCTACGGCTCCGGCGCGACCTGGGGCGCGGCGCTGTACCGCAAACCTGAGG
AGGTGAACCGGCCATGTTGA
```

*pqsE* (SEQ ID NO:5)
```
ATGTTGAGGCTTTCGGCTCCCGGTCAACTGGATGATGACCTGTGCCTGTTGGGGGACGTCCAGGTGCCGGT
GTTCCTGCTGCGTCTCGGTGAGGCGAGCTGGGCGCTGGTTGAAGGAGGGATCAGCCGGGATGCCGAATTGG
TTTGGCGGACCTGTGCCGCTGGGTCGCCGACCCGTCCCAGGTGCACTACTGGCTGATCACCCACAAGCAC
TACGACCACTGCGGCCTGCTGCCCTACCTGTGTCCGCGGCTGCCGAACGTACAGGTCCTGGCGTCCGAGCG
GACCTGCCAGGCCTGGAAGTCGGAAAGCGCGGTGCGGGTGGTCGAGCGCTTGAACCGGCAACTGTTGCGTG
CGGAGCAGCGGTTGCCCGAGGCCTGTGCCTGGGACGCTCTGCCGGTTCGCGCGGTGGCCGACGGCGAGTGG
CTGGAGCTGGGACCGCGGCATCGCCTGCAGGTCATAGAGGCCCACGGCCACAGCGACGATCACGTGGTTTT
CTACGACGTGCGACGCCGACGCCTGTTCTGCGGCGATGCCCTGGGCGAGTTCGACGAGGCAGAGGGGGTGT
GGCGGCCGCTGGTGTTCGACGACATGGAGGCTTACCTGGAGTCCCTGGAACGTCTGCAGCGTCTGCCGACC
CTGCTGCAACTGATCCCGGGACACGGCGGCCTGCTGCGGGGCGGCTGGCCGCGGATGGGGCCGAGTCGGC
CTATACCGAGTGTCTGCGCCTGTGCCGGCGGTTGCTCTGGCGCCAGTCCATGGGCGAATCCCTCGACGAAC
TGAGCGAGGAGCTGCACCGCGCCTGGGTGGGCAGAGCGTCGACTTCCTGCCCGGCGAACTGCACCTGGGG
AGCATGCGCCGGATGCTGGAGATTCTCTCCCGCCAGGCGCTGCCTCTGGACTGA
```

*pqsH* (SEQ ID NO:6)
```
ATGACCGTTCTTATCCAGGGGGCCGGGATCGCCGGCCTGGCGCTGGCGCGCGAATTCACCAAGGCAGGCAT
CGACTGGCTGCTGGTCGAGCGGGCCAGCGAGATCAGGCCCATCGGTACCGGCATCACCCTGGCGAGCAATG
CGTTGACGGCGTTGTCCAGCACCCTGGATCTCGACCGGCTGTTCCGCCGTGGCATGCCGTTGGCCGGCATC
AACGTATACGCCCACGACGGTTCGATGCTGATGTCGATGCCTTCCAGTCTGGGTGGGAATTCCCGCGGCGG
CCTGGCGTTGCAGCGCCACGAACTGCATGCGGCGCTACTGGAGGGGCTGGATGAGTCGCGCATTCGGGTCG
GGGTCTCCATCGTGCAGATCCTCGACGGACTCGACCACGAACGCGTGACCCTGAGCGACGGCACTGTCCAC
GACTGTTCGCTGGTGGTCGGTGCGGATGGCATTCGTTCGAGCGTGCGACGTTATGTCTGGCCGGAGGCGAC
CTTGCGTCATTCCGGCGAAACCTGCTGGCGCCTGGTCGTTCCCCATCGGCTGGAGGACGCCGAGCTGGCGG
GAGAGGTCTGGGGGCACGGCAAGCGCCTCGGCTTCATCCAGATCAGCCCGCGCGAGATGTATGTCTACGCG
ACCCTGAAGGTGCGCCGGGAGGAGCCCGAGGACGAGGAGGGCTTCGTAACCCCGCAACGGCTGGCCGCCCA
CTACGCGGACTTCGACGGCATCGGCGCGAGCATCGCCCGGCTCATACCGAGCGCCACCACGCTGGTGCACA
ACGACCTCGAGGAGTTGGCCGGCGCCTCCTGGTGCCGCGGACGGGTAGTGCTGATCGGTGACGCCGCACAC
```

Figure 11B

```
GCCATGACGCCGAACCTGGGGCAGGGCGCGGCCATGGCCCTGGAGGACGCCTTCCTGCTGGCGCGCCTGTG
GTGCCTGGCGCCGCGCGCCGAGACGCTGATCCTGTTCCAGCAGCAACGCGAGGCGCGGATCGAGTTCATCA
GGAAGCAATCCTGGATCGTCGGCCGCCTTGGTCAGTGGGAATCGCCCTGGAGCGTCTGGCTGAGGAATACC
CTCGTTCGCCTGGTGCCGAATGCCAGTCGCAGGCGCCTCCACCAGCGTCTTTTCACCGGTGTCGGTGAGAT
GGCCGCACAGTAG
``` pqsL (SEQ ID NO:7)
```
ATGACGGACAACCATATCGATGTACTGATCAACGGCTGCGGCATCGGCGGGGCGATGCTCGCCTACCTGCT
CGGCCGCCAGGGCCACCGCGTGGTGGTAGTGGAACAGGCACGGCGCGAACGCGCGATCAACGGCGCCGACC
TGCTCAAGCCGGCCGGCATCCGGGTGGTCGAGGCGGCCGGGTTGTTGGCCGAGGTGACCCGTCGCGGTGGG
CGGGTCCGCCATGAGCTGGAGGTCTATCACGACGGCGAGCTGCTTCGCTATTTCAACTATTCCAGCGTCGA
CGCGCGCGGCTATTTCATCCTCATGCCCTGCGAGTCGCTGCGCCGCCTGGTACTGGAAAAAATCGACGGCG
AAGCGACCGTCGAGATGCTGTTCGAGACCCGCATCGAAGCGGTGCAGCGCGACGAGCGCCACGCGATCGAC
CAGGTGCGCCTGAACGACGGCCGCGTGCTGCGTCCGCGGGTGGTGGTGGGAGCCGACGGTATCGCCTCCTA
CGTGCGCCGCCGGCTGCTCGATATCGATGTGGAACGCCGCCCCTACCCGTCGCCGATGCTGGTCGGCACCT
TCGCCCTGGCGCCCTGCGTGGCCGAGCGCAACCGCCTGTACGTGGACTCGCAGGGCGGGCTGGCCTACTTC
TATCCGATCGGTTTCGACCGCGCGCGACTGGTGGTGAGCTTCCCCAGGGAGGAGGCGCGCGAGCTGATGGC
CGACACCCGCGGCGAGTCGCTGCGCCGGCGCTTGCAACGCTTCGTCGGCGACGAGAGCGCCGAGGCGATCG
CCGCCGTCACCGGCACTTCGCGCTTCAAGGGCATCCCCATCGGCTACCTGAACCTGGACCGCTACTGGGCG
GACAACGTGGCGATGCTCGGCGACGCCATCCACAACGTGCATCCGATCACCGGCCAGGGCATGAACCTGGC
CATCGAGGACGCCAGCGCCCTGGCCGACGCCCTCGACCTGGCCTTGCGCGACGCCTGCGCGCTGGAGGATG
CCCTGGCCGGCTACCAGGCCGAGCGCTTCCCGGTGAACCAGGCGATCGTCTCCTATGGCCATGCGTTGGCC
ACCAGCCTGGAGGATCGCCAGCGCTTCGCCGGGGTCTTCGACACCGCCCTGCAGGGCAGCAGCCGTACGCC
GGAAGCCCTGGGCGGCGAGCGCTCCTACCAGCCGGTGCGGTCGCCGGCGCCGCTCGGCTGA
```

PqsA (SEQ ID NO:8)
```
MSTLANLTEVLFRLDFDPDTAVYHYRGQTLSRLQCRTYILSQASQLARLLKPGDRVVLALNDSPSLACLFL
ACIAVGAIPAVINPKSREQALADIAADCQASLVVREADAPSLSGPLAPLTLRAAAGRPLLDDFSLDALVGP
ADLDWSAFHRQDPAAACFLQYTSGSTGAPKGVMHSLRNTLGFCRAFATELLALQAGDRLYSIPKMFFGYGM
GNSLFFPWFSGASALLDDTWPSPERVLENLVAFRPRVLFGVPAIYASLRPQARELLSSVRLAFSAGSPLPR
GEFEFWAAHGLEICDGIGATEVGHVFLANRPGQARADSTGLPLPGYECRLVDREGHTIEEAGRQGVLLVRG
PGLSPGYWRASEEQQARFAGGWYRTGDLFERDESGAYRHCGREDDLFKVNGRWVVPTQVEQAICRHLPEVS
EAVLVPTCRLHDGLRPTLFVTLATPLDDNQILLAQRIDQHLAEQIPSHMLPSQLHVLPALPRNDNGKLARA
ELRHLADTLYHDNLPEERAC
```

PqsB (SEQ ID NO:9)
```
MLIQAVGVNLPPSYVCLEGPLGGERPRAQGDEMLMQRLLPAVREALDEAAVKPEEIDLIVGLALSPDHLIE
NRDIMAPKIGHPLQKVLGANRAHVFDLTDSSLARALYVVDTLASDQGYRNVLVVRGESSQGLEVDSESGFA
LADGALALLCRPTGKAAFRRGALGGDPAQEWLPLSIPLNTDIRQVGDVKGHLNLPAQPGLPEAVRAGFTRL
AGDFPQLNWVREEWFGQGRPDGRCLGPFELASQLRAAQRDRLDELLLISFDPFGMVVEGVTLELAGEAHA
```

PqsC (SEQ ID NO:10)
```
MHKVKLAAITCELPARSYENDDPVFAAVPDLSESWWQFWGVNRRGYFDPRNGENEFSLVVRAAERLLRSSD
TAPDSVDMLICSASSPIMTDAGDVLPDLRGRLYPRMANVLSKQLGLSRALPLDSQMECASFLLNLRLAASM
IRQGKAEKVLVVCSEYISNLLDFTSRTSTLFADGCAVALLTRGDDDSCDLLASAEHSDATFYEVATGRWRL
PENPTGEAKPRLYFSLFSDGQNKMASFVPTNVPIAMRRALEKAGLGSDDIDYFVFHQPAPFLVKAWAEGIG
ARPEQYQLTMGDTGVMISVSIPYTLMTGLREGKIRPGDRIVMAGAATGWGFAAQVWQLGEVLVC
```

Figure 11C

PqsD (SEQ ID NO:11)
MGNPILAGLGFSLPKRQVSNHDLVGRINTSDEFIVERTGVRTRYHVEPEQAVSALMVPAARQAIEAAGLLP
EDIDLLLVNTLSPDHHDPSQACLIQPLLGLRHIPVLDIRAQCSGLLYGLQMARGQILAGLARHVLVVCGEV
LSKRMDCSDRGRNLSILLGDGAGAVVVSAGESLEDGLLDLRLGADGNYFDLLMTAAPGSASPTFLDENVLR
EGGGEFLMRGRPMFEHASQTLVRIAGEMLAAHELTLDDIDHVICHQPNLRILDAVQEQLGIPQHKFAVTVD
RLGNMASASTPVTLAMFWPDIQPGQRVLVLTYGSGATWGAALYRKPEEVNRPC

PqsE (SEQ ID NO:12)
MLRLSAPGQLDDDLCLLGDVQVPVFLLRLGEASWALVEGGISRDAELVWADLCRWVADPSQVHYWLITHKH
YDHCGLLPYLCPRLPNVQVLASERTCQAWKSESAVRVVERLNRQLLRAEQRLPEACAWDALPVRAVADGEW
LELGPRHRLQVIEAHGHSDDHVVFYDVRRRLFCGDALGEFDEAEGVWRPLVFDDMEAYLESLERLQRLPT
LLQLIPGHGGLLRGRLAADGAESAYTECLRLCRRLLWRQSMGESLDELSEELHRAWGGQSVDFLPGELHLG
SMRRMLEILSRQALPLD

PqsH (SEQ ID NO:13)
MTVLIQGAGIAGLALAREFTKAGIDWLLVERASEIRPIGTGITLASNALTALSSTLDLDRLFRRGMPLAGI
NVYAHDGSMLMSMPSSLGGNSRGGLALQRHELHAALLEGLDESRIRVGVSIVQILDGLDHERVTLSDGTVH
DCSLVVGADGIRSSVRRYVWPEATLRHSGETCWRLVVPHRLEDAELAGEVWGHGKRLGFIQISPREMYVYA
TLKVRREEPEDEEGFVTPQRLAAHYADFDGIGASIARLIPSATTLVHNDLEELAGASWCRGRVVLIGDAAH
AMTPNLGQGAAMALEDAFLLARLWCLAPRAETLILFQQQREARIEFIRKQSWIVGRLGQWESPWSVWLRNT
LVRLVPNASRRRLHQRLFTGVGEMAAQ

PqsL (SEQ ID NO:14)
MTDNHIDVLINGCGIGGAMLAYLLGRQGHRVVVVEQARRERAINGADLLKPAGIRVVEAAGLLAEVTRRGG
RVRHELEVYHDGELLRYFNYSSVDARGYFILMPCESLRRLVLEKIDGEATVEMLFETRIEAVQRDERHAID
QVRLNDGRVLRPRVVVGADGIASYVRRRLLDIDVERRPYPSPMLVGTFALAPCVAERNRLYVDSQGGLAYF
YPIGFDRARLVVSFPREEARELMADTRGESLRRRLQRFVGDESAEAIAAVTGTSRFKGIPIGYLNLDRYWA
DNVAMLGDAIHNVHPITGQGMNLAIEDASALADALDLALRDACALEDALAGYQAERFPVNQAIVSYGHALA
TSLEDRQRFAGVFDTALQGSSRTPEALGGERSYQPVRSPAPLG

***pqsA-E* operon promoter (including ATG start site of *pqsA*) (SEQ ID NO:15)**
GTAGGTGTCCTCTTCGGCAGGCTCGCCCAGTGTACTACGCAATGGGATTTCAACAGGGAAGCCTGCAAATG
GCAGGCGAGGCGGGGCGGAGCGCTATCGGCCCGATGGATGGCCGCCTGCTTCCAGGCATGCCGTCGCCCCC
TTGGAGCCCAGGCCGAGCGCCTCGAACTGTGAGATTTGGGAGGCGATTTGCCGAGCAAAGTGGGTTGTCAT
TGGTTTGCCATCTCATGGGTTCGGACGAGGCCTCGAGCAAGGGTTGTAACGGTTTTGTCTGGCCAATGGG
CTCTTGCGTAAAAAGGCTGCCGCCCTTCTTGCTTGGTTGCCGTTCTCGGATCCCGCGCAGCCCGGTGGGTG
TGCCAAATTTCTCGCGGTTTGGATCGCGCCGATTGCCGCGGCCTACGAAGCCCGTGGTTCTTCTCCCCGAA
ACTTTTTCGTTCGGACTCCGAATATCGCGCTTCGCCCAGCGCCGCTAGTTTCCCGTTCCTGACAAAGCAAG
CGCTCTGGCTCAGGTATCTCCTGATCCGGATGCATATCGCTGAAGAGGGAACGTTCTGTCATG

***mvfR* (SEQ ID NO:16)**
ATGCCTATTCATAACCTGAATCACGTGAACATGTTCCTCCAGGTCATCGCCTCCGGTTCGATTTCCTCCGC
TGCGCGGATCCTGCGCAAGTCGCACACCGCGGTCAGCTCGGCGGTCAGCAACCTGGAAATCGACCTGTGCG
TGGAGCTGGTCCGTCGGGACGGCTACAAGGTCGAACCCACCGAGCAGGCGCTTCGCCTGATCCCTTACATG
CGCAGCCTGCTGAACTACCAGCAGCTGATCGGCGACATCGCCTTCAATCTCAACAAGGGTCCGCGCAATCT

Figure 11D

```
CCGGGTGCTGCTGGACACCGCCATCCCGCCGTCGTTCTGCGATACGGTGAGCAGCGTACTGCTCGACGATT
TCAACATGGTCAGCCTGATACGCACCTCGCCCGCCGATAGCCTGGCGACGATCAAGCAGGACAACGCGGAA
ATCGATATCGCCATCACCATCGACGAGGAACTGAAGATCTCCCGCTTCAACCAGTGCGTGCTCGGCTACAC
CAAGGCGTTCGTCGTCGCCCATCCGCAGCACCCGTTGTGCAATGCCTCCCTGCACAGCATCGCGAGCCTGG
CCAATTACCGGCAGATCAGCCTCGGCAGCCGCTCCGGGCAGCATTCGAACCTGCTGCGGCCGGTCAGCGAC
AAGGTGCTCTTCGTGGAAAACTTCGACGACATGCTGCGTCTGGTGGAAGCCGGCGTCGGATGGGGCATCGC
GCCGCATTATTTCGTCGAGGAACGCCTGCGCAACGGTACCCTGGCAGTCCTCAGCGAACTCTACGAACCGG
GCGGCATCGACACCAAGGTGTATTGCTACTACAACACCGCGCTGGAATCCGAGCGCAGCTTCCTGCGCTTT
CTCGAAAGCGCCCGCCAGCGCCTGCGCGAACTCGGCCGCCAGCGTTTCGACGATGCGCCGGCCTGGCAACC
GAGCATCGTCGAAACGGCGCAGCGCCGCTCAGGCCCGAAGGCGCTCGCGTACCGCCAGCGCGCCGCACCAG
AGTAG
```

MvfR ((SEQ ID NO:17)
```
MPIHNLNHVNMFLQVIASGSISSAARILRKSHTAVSSAVSNLEIDLCVELVRRDGYKVEPTEQALRLIPYM
RSLLNYQQLIGDIAFNLNKGPRNLRVLLDTAIPPSFCDTVSSVLLDDFNMVSLIRTSPADSLATIKQDNAE
IDIAITIDEELKISRFNQCVLGYTKAFVVAHPQHPLCNASLHSIASLANYRQISLGSRSGQHSNLLRPVSD
KVLFVENFDDMLRLVEAGVGWGIAPHYFVEERLRNGTLAVLSELYEPGGIDTKVYCYYNTALESERSFLRF
LESARQRLRELGRQRFDDAPAWQPSIVETAQRRSGPKALAYRQRAAPE
```

Figure 11E

| (% of PA14) | mvfR | phnAB | pqsA | pqsB | pqsE | mvfR compl. | lasR |
|---|---|---|---|---|---|---|---|
| HHQ | 0 | 48 ± 5 | 0 | 0 | 49 ± 4 | 1017 ± 247 | 250 ± 11 |
| HHQ N-oxide | 0 | 110 ± 17 | 0 | 0 | 148 ± 29 | 200 ± 41 | 45 ± 8 |
| PQS | 0 | 76 ± 11 | 0 | 0 | 90 ± 13 | 247 ± 65 | 23 ± 3 |
| HNQ | 0 | 68 ± 5 | 0 | 0 | 84 ± 5 | 502 ± 106 | 551 ± 262 |
| HNQ N-oxide | 0 | 91 ± 15 | 0 | 0 | 135 ± 20 | 286 ± 52 | 41 ± 3 |
| diHNQ | 0 | 128 ± 21 | 0 | 0 | 160 ± 27 | 156 ± 49 | 19 ± 3 |
| AA | 0 | 90 ± 51 | 458 ± 221 | 188 ± 102 | 24 ± 17 | 0 | 6 ± 1 |
| Pyocyanin | <10 | 24 ± 3 | <10 | <10 | <10 | 177 ± 26 | NT |

|  | PQS (µg/ml) | β-gal activity (MU)[†] |
|---|---|---|
| lasR⁻ | 2.1 ± 0.1 | 63.6 ± 2.6 |
| lasR⁻ + mvfR⁻ | 5.2 ± 1.8 | 110.5 ± 4.3 |
| Ratio[*] | 5.0 ± 1.8 | 3.5 ± 0.2 |

FIGURE 14

|      | $\beta$-gal activity (MU)[†] | |
|------|------|------|
|      | PA14 | lasR[-†] |
| -HHQ | 371 ± 8 | 78.7 ± 1.5 |
| +HHQ | 473 ± 23 | 83.7 ± 0.2 |

METHODS FOR IDENTIFYING CANDIDATE COMPOUNDS FOR TREATING, REDUCING, OR PREVENTING PATHOGENIC INFECTIONS

CROSS-REFERENCE TO RELATED APPLICATIONS

This application is the U.S. National Stage of International Application No. PCT/US2005/002174, filed Jan. 21, 2005, which in turn, claims the benefit of U.S. Provisional Application No. 60/538,278, filed Jan. 21, 2004, and U.S. Provisional Application No. 60/538,361, filed Jan. 22, 2004.

BACKGROUND OF THE INVENTION

The invention relates to drug-screening assays for evaluating and identifying compounds capable of affecting pathogenicity and virulence of a pathogen.

Pathogens employ a number of genetic strategies to cause infection and, occasionally, disease in their hosts. The expression of microbial pathogenicity is dependent upon complex genetic regulatory circuits. Knowledge of the themes in microbial pathogenicity is necessary for understanding pathogen virulence mechanisms and for the development of new "anti-virulence" or "anti-pathogenic" agents, which are needed to combat infection and disease.

The mechanism of pathogenesis and the host defense is a field of intense investigation. Antibiotics have been an effective tool to treat unwanted bacterial infections. However, due to the increasing incidence of resistance to current antibiotics, new antibiotics are needed. Antibiotics that target non-essential genes are desirable because there is limited, if any, selection pressure on these genes since they are not required for the survival of the bacteria. Thus, bacteria are less likely to develop resistance to antibiotics that target these genes.

In nature, most bacteria live not as individual cells but as pseudo-multicellular organisms that coordinate their population behavior via small extracellular signal molecules. Under appropriate conditions, these molecules are released into the environment, taken up, and responded to by surrounding cells (Fuqua et al., *Annu. Rev. Genet.* 35, 439-68, 2001; Miller et al., *Annu. Rev. Microbiol.* 55, 165-199, 2001; Withers et al., *Curr. Opin. Microbiol.* 4, 186-193, 2001). 'Quorum sensing' (QS), is the archetypal intercellular communication system used by many bacterial species to regulate their gene expression in response to cell density. Using this regulatory system, all the individual bacterial cells behave coordinately and synergistically as a community, for example, in growth dynamics and resource utilization (Fuqua et al., *J. Bacteriol.* 176, 269-275, 1994). A common feature of all QS systems is the transcriptional activation and repression of a large regulon of QS-controlled genes when a minimal threshold concentration of a specific autoinducer is reached.

The QS system used by Gram-negative bacteria is mediated by the extracellular signaling molecules, N-acyl-L-homoserine lactones (AHLs) (Withers et al., *Curr Opin Microbiol* 4, 186-193, 2001; Fuqua et al., *Annu Rev Genet* 35: 439-68, 2001). The versatile and ubiquitous opportunistic pathogen *Pseudomonas aeruginosa* is one of the best-studied models of AHL-mediated QS. In this species, two separate autoinducer synthase/transcriptional regulator pairs, LasRI and RhlRI, modulate the expression of several genes, including many virulence factors, in response to increasing concentrations of the specific signaling molecules oxo-$C_{12}$—HSL and $C_4$—HSL (Pesci et al., in *Cell-cell signaling in bacteria*, eds., 1999; Van Delden et al., *Emerg. Infect. Dis.* 4, 551-560, 1998).

*P. aeruginosa* also produces a cell-to-cell signal distinct from AHLs: 3,4-dihydroxy-2-heptylquinoline, called the PQS signal (Pesci et al., *Proc. Natl. Acad. Sci. USA* 96, 11229-11234, 1999). PQS serves as a signaling molecule regulating the expression of a subset of genes belonging to the QS regulon, including the phz and hcn operons. PQS functions in the QS hierarchy by linking a regulatory cascade between the las and the rhl systems (McKnight et al., *J. Bacteriol.* 182, 2702-2708, 2000). That maximal PQS production occurs at the end of the exponential growth phase (Lépine et al., *Biochim. Biophys. Acta* 1622, 36-40, 2003) supports the hypothesis that PQS acts as a secondary regulatory signal for a subset of QS-controlled genes. Although PQS has no antibiotic activity (Pesci et al., *Proc. Natl. Acad. Sci. USA* 96, 11229-11234, 1999), it belongs to a family of poorly characterized antimicrobial *P. aeruginosa* products, the 'pyo' compounds, originally described in 1945, which are derivatives of 4-hydroxy-2-alkylquinolines (HAQs) (Hays et al., *J. Biol. Chem.* 159, 725-750, 1945; Wells, *J. Biol. Chem.* 196, 331-340, 1952). The QS-associated *P. aeruginosa* transcriptional regulator, MvfR, is also required for the production of several secreted compounds, including virulence factors and PQS (Cao et al., *Proc. Natl. Acad. Sci. USA* 98, 14613-8, 2001; Rahme et al., *Proc. Natl. Acad. Sci. USA* 94, 13245-13250, 1997). MvfR controls the synthesis of anthranilic acid (AA), a PQS precursor (Calfee et al., *Proc. Natl. Acad. Sci. USA* 98, 11633-11637, 2001), by positively regulating the transcription of phnAB, which encodes an anthranilate synthase (Cao et al., *Proc. Natl. Acad. Sci. USA* 98, 14613-8, 2001).

This pathway represents a candidate target for the pharmacological intervention of *P. aeruginosa* mediated infections.

SUMMARY OF THE INVENTION

The present invention provides screening methods to identify compounds useful (e.g., a peptide, polypeptide, synthetic organic molecule, naturally occurring organic molecule, nucleic acid molecule, or component thereof) for the treatment, prevention, or reduction of pathogenic infections caused, for example, by *Pseudomonas aeruginosa*. Using such agents as lead compounds, for example, the present screening methods also allow the identification of further novel, specific agents that function to treat, reduce, or prevent pathogenic infections.

According to one approach, candidate compounds are added at varying concentrations to the culture medium of pathogenic cells (any pathogenic cell, such as those that infect mammals (e.g., *Pseudomonas aeruginosa* such as PA14 or PAO1) or plants) after which the production of an HAQ molecule, HHQ molecule, derivatives or precursors thereof is measured using any standard method known in the art or described herein. For example, the production of the HAQ molecule is determined. Exemplary HAQ molecules, HHQ molecules, derivatives thereof, or precursors thereof are provided in FIG. 5 and FIG. 2.

Alternatively, the screening methods of the invention may be used to identify candidate compounds to decrease the production of an HAQ molecule, an HHQ molecule, a derivative thereof, or a precursor thereof (thereby decreasing the production of PQS, in turn reducing the virulence of a pathogenic cell) by their ability to reduce, treat, or prevent a pathogenic infection. Such reduction is desirably at least 10%, 20%, 30%, 40%, 50%, 60%, 70%, 80%, 90%, 95%, or 100% relative to an untreated control.

Alternatively, the screening method may involve contacting a population of pathogenic cells with a candidate compound, culturing the population of cells for a predetermined amount of time, and collecting the supernatant from the population of cells. The collected supernatant is next placed on a second population of cells expressing a PqsH protein (or a chemical derivative thereof) after which the production of PQS from this second population is measured by any method known in the art. If the candidate compound reduces the production of PQS in this population of cells relative to a control population that has been contacted with supernatant collected from pathogenic cells cultured in the absence of a candidate compound, this candidate compound is identified as being useful for treating, preventing, or reducing a pathogenic infection by virtue of its ability to interfere with the HHQ biosynthesis pathway. The PqsH protein used in this assay may be encoded by a nucleic acid of SEQ ID NO: 6 or by a nucleic acid molecule that binds under stringent conditions to SEQ ID NO: 6 or a sequence complementary thereto. Alternatively, the PqsH protein is substantially identical to the amino acid sequence of SEQ ID NO: 13. Pathogenic cells may either endogenously express PqsH or may alternatively be genetically engineered by any standard technique known in the art (e.g., transfection and viral infection) to overexpress PqsH. The effect of a candidate compound on the production of PQS may be tested by radioactive and non-radioactive binding assays, competition assays, and signaling assays.

Ultimately, the screening assay of the invention may be carried out, for example, in a cell-free system. If desired, one of the Pqs proteins, HAQ molecules, HHQ molecules, a derivative or precursor thereof, or the candidate compound may be immobilized on a support or may have a detectable group.

Alternatively, or in addition, candidate compounds may be screened for those which specifically bind to and thereby reduce HAQ or HHQ activity or levels. The efficacy of such a candidate compound is dependent upon its ability to interact with such molecules. Such an interaction can be readily assayed using any number of standard binding techniques and functional assays (e.g., Ausubel et al., *Current Protocols in Molecular Biology*, 2004, John Wiley and Sons). For example, a candidate compound may be tested in vitro for interaction and binding with an HAQ molecule, HHQ molecule, a precursor or derivative thereof, and its ability to reduce HAQ or HHQ activity or levels may be assayed by any standard assays described in the art or those described herein.

Alternatively, the invention also provides a method of identifying a candidate compound by contacting a candidate compound, a Pqs protein (e.g., pqsA, pqsB, pqsC, pqsD, pqsE, pqsH, and pqsL protein), and an HAQ or HHQ molecule (or a derivative/precursor thereof) capable of binding the Pqs protein under conditions that allow binding. If HHQ is used in this method instead of an HAQ molecule, a PqsH protein is used. Binding of this Pqs protein to the HAQ molecule or HHQ molecule (or a derivative/precursor thereof) is next measured such that a decrease in binding effected by the candidate compound identifies a candidate compound useful for treating, reducing, or preventing a pathogenic infection. The Pqs protein may contain an amino acid sequence substantially identical to any one of SEQ ID NOs: 8-14, or may alternatively be encoded by a nucleic acid molecule that is substantially identical to or that hybridizes under stringent conditions to any one of SEQ ID NOs: 1-7.

Alternatively, the invention also provides a method of identifying a candidate compound by contacting a candidate compound, an MvfR protein, a nucleic acid sequence substantially identical to the nucleic acid of SEQ ID NO:15 or with a nucleic acid molecule that binds under stringent conditions to SEQ ID NO:15 or a sequence complementary thereto or fragment thereof (e.g., the lysR-box sequence). Binding of MvfR to this nucleic acid is next measured such that a decrease in binding effected by the candidate compound identifies a candidate compound useful for treating, reducing, or preventing a pathogenic infection. The MvfR protein may contain an amino acid sequence substantially identical to any one of SEQ ID NO:17, or may alternatively be encoded by a nucleic acid molecule that is substantially identical to or that hybridizes under stringent conditions to any one of SEQ ID NO:16.

In still another embodiment, the invention also provides a method of identifying a candidate compound by contacting a candidate compound, a mutant pqs strain (e.g. pqsA mutant) strain of a cell (for example, any pathogenic cell, such as those that infect mammals (e.g., *Pseudomonas aeruginosa* such as PA14 or PAO1) or plants) containing a pqs-reporter (e.g., a pqsA-LacZ reporter) and a PQS molecule. The output level of the reporter construct is next measured such that a decrease in output effected by the candidate compound identifies a candidate compound useful for treating, reducing, or preventing a pathogenic infection.

In addition, the invention also provides a method of identifying a candidate compound by contacting a candidate compound, a nucleic acid of SEQ ID NO:15 or by contacting a nucleic acid molecule that binds under stringent conditions to SEQ ID NO:15 or a sequence complementary thereto or fragment thereof (e.g. a fragment containing a lysR-box). The binding of this nucleic acid to the candidate compound identifies a candidate compound useful for treating, reducing, or preventing a pathogenic infection.

Screening for new inhibitors and optimization of lead compounds may be assessed, for example, by assessing their ability to function as anti-pathogenic agents (e.g., as described herein). Compounds isolated by this approach may also be used, for example, as therapeutics to treat, reduce, or prevent pathogenic infections. Compounds which are identified as binding to HHQ or HAQ (or a derivative/precursor thereof) with an affinity constant less than or equal to 10 mM are considered particularly useful in the invention.

Ultimately, the candidate compounds identified by the present screening methods may be used to treat, prevent, or reduce pathogenic infections in plants and mammals caused, for example, by *Pseudomonas aeruginosa*.

As used herein, by "Pqs protein" is meant any polypeptide that exhibits an activity common to its related, naturally occurring Pqs polypeptide. According to this invention, such proteins include any of the Pqs proteins, including PqsA, PqsB, PqsC, PqsD, PqsE, PqsH, and PqsL. The Pqs protein of the invention may participate in bacterial quorum sensing, a process used by bacteria to coordinate their population behavior through the action of extracellular signal molecules. The naturally occurring PqsA-E enzymes typically participate in this process by catalyzing the biosynthesis of the extracellular signal molecules, 4-hydroxy-2-alkylquinolines (HAQs). PqsH protein is typically involved in the production of PQS from HHQ. Such activities are shown in FIG. 5. Desirably, the Pqs protein of the invention is associated with such activity and in turn, increases pathogenic virulence.

Accordingly, the Pqs protein of the invention is substantially identical to any of the naturally occurring Pqs proteins, including PqsA, PqsB, PqsC, PqsD, PqsE, PqsH, and PqsL. Thus, the Pqs protein may be at least 5%, 10%, 20%, 30%, 40%, 50%, 60%, 70%, 80%, 90%, 95%, 100% identical to any of the amino acid sequence of SEQ ID NOs: 8-14. Other exemplary Pqs proteins may be found in Genbank Accession Numbers ZP_00138572, ZP_00138573, ZP_00138574, ZP_00138575, ZP_00138576, ZP_00135896, and ZP_00137677. Alternatively, the Pqs protein is encoded by a nucleic acid molecule that is at least 5%, 10%, 20%, 30%, 40%, 50%, 60%, 70%, 80%, 90%, 95%, 100% identical to any one of the nucleic acid sequence of SEQ ID NOs: 1-7 or by a nucleic acid molecule that hybridizes under stringent conditions to any one of the nucleic acids of SEQ ID NOs: 1-7 or the complementary sequence thereto. Preferably, the Pqs protein increases the biosynthesis of HAQs, HHQ, or PQS or alternatively, increases pathogenic virulence by at least 5%, 10%, 20%, 30%, 40%, 50%, 60%, 70%, 80%, 90%, or more than 100% above control levels as measured by any standard method known in the art.

By "reduce the level or activity of Pqs protein" is meant to reduce the expression level or the biological activity of Pqs relative to the expression level or biological activity of Pqs in an untreated control. According to this invention, such level or activity is modulated by at least 10%, 20%, 30%, 40%, 50%, 60%, 70%, 80%, 90%, 100%, or even greater than 100%, relative to an untreated control. Desirably, pathogenic infections are treated, prevented, or reduced if the biological activity or level of Pqs protein is reduced in a mammal or plant.

By "reduce the production of an HAQ molecule, HHQ molecule, a derivative thereof, or a precursor thereof" is meant to reduce the level or the biological activity of such HAQ molecule, HHQ molecule, (or a derivative/precursor thereof) relative to the expression level or biological activity of the corresponding molecules in an untreated control. According to this invention, such level or activity is reduced by at least 10%, 20%, 30%, 40%, 50%, 60%, 70%, 80%, 90%, 100%, or even greater than 100%, relative to an untreated control as measured by any method known in the art or described herein. For example, the level of HAQ may be assayed by measuring HAQ antimicrocibial activity. HHQ levels may be determined by contacting a test sample with a population of cells expressing a PqsH protein and detecting the production level of PQS that results from such contacting. Alternatively, such reduction may also be determined by assaying the virulence of a pathogenic cell. Accordingly, a useful candidate compound reduces the virulence of a pathogenic cell. Desirably, pathogenic infections are treated, prevented, or reduced if the production or level of an HAQ or HHQ (or a derivative/precursor thereof) is reduced in a mammal or plant by interfering with PQS production, in turn reducing the virulence of pathogenic cells. Such exemplary molecules are shown in FIGS. 2 and 5.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof.

By "nucleic acid molecule" is meant multiple nucleotides, each of which contains a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G). As used herein, the term refers to oligoribonucleotides as well as oligodeoxyribonucleotides. The nucleic acid molecules of the invention also include polynucleosides (i.e. a polynucleotide lacking the phosphate) and any other organic base-containing polymer. Nucleic acid molecules may be obtained from existing nucleic acid sources (e.g. genomic or cDNA), but if desired, may be synthetic (e.g. produced by oligonucleotide synthesis).

By "polypeptide" is meant any chain of amino acids, regardless of length or post-translational modification (for example, glycosylation or phosphorylation).

By "substantially identical" is meant a polypeptide or nucleic acid molecule exhibiting at least 25% identity to a reference amino acid sequence (for example, any one of the amino acid sequences described herein) or nucleic acid sequence (for example, any one of the nucleic acid sequences described herein). Preferably, such a sequence is at least 30%, 40%, 50%, 60%, 70%, more preferably 80%, 81%, 82%, 83%, 84%, 85% identical, and most preferably 90%, 92%, 94%, 95%, 96%, 97%, 98%, or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "pathogenic infection" is meant any infection caused by the presence of a microbial agent, such as a bacterium. According to this invention, pathogens may infect a mammal (e.g., human) or a plant. Bacterial infections may be caused by Gram-positive and Gram-negative agents (e.g., *Pseudomonas aeruginosa*), that may or may not display antibiotic resistance. Pathogenic infections may or may not be symptomatic.

By "treating, reducing, or preventing a pathogenic infection" is meant reducing such infection before or after it has occurred. As compared with an equivalent untreated control, such reduction or degree of prevention is at least 5%, 10%, 20%, 40%, 50%, 60%, 80%, 90%, 95%, or 100% as measured by any standard technique that detects the level of the pathogen. Typically, a patient who is being treated for a pathogenic infection is one who a medical practitioner has diagnosed as having such a condition. Diagnosis may be performed by any suitable means known in the art or described herein. Typically, infections are diagnosed by the evaluation of symptoms, or alternatively, by the detection of the pathogen in a biological specimen in a culture assay. Similarly, a reduction in a pathogenic infection may be measured by monitoring pathogenic symptoms in a patient exposed to a candidate compound or extract, a decrease in the level of symptoms relative to the level of pathogenic symptoms in a patient not exposed to the compound indicating compound-mediated inhibition of the pathogen.

A patient in whom the development of a pathogenic infection is being prevented may or may not have received such a diagnosis. One skilled in the art will understand that these patients may have been subjected to the same standard tests as described above or may have been identified, without examination, as one at high risk due to the presence of one or more risk factors (e.g., contact with infected patient).

By "an effective amount" is meant an amount of a compound, alone or in a combination, required to treat, reduce, or prevent a pathogenic infection. The effective amount of active compound(s) varies depending upon the route of administration, age, body weight, and general health of the subject. Ultimately, the attending physician or veterinarian will decide the appropriate amount and dosage regimen.

The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20th edition, (ed. A R Gennaro), Mack Publishing Co., Easton, Pa., 2000.

By "isolated nucleic acid molecule" is meant a nucleic acid (e.g., a DNA) that is free of the genes which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By a "substantially pure polypeptide" is meant a polypeptide of the invention that has been separated from components which naturally accompany it. Typically, the polypeptide is substantially pure when it is at least 60%, by weight, free from the proteins and naturally occurring organic molecules with which it is naturally associated. Preferably, the preparation is at least 75%, more preferably at least 90%, and most preferably at least 99%, by weight, a polypeptide of the invention. A substantially pure polypeptide of the invention may be obtained, for example, by extraction from a natural source (for example, a pathogen); by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "pathogenic virulence factor" is meant a cellular component (e.g., a protein such as a transcription factor, as well as the gene which encodes such a protein) without which the pathogen is incapable of causing disease or infection in a eukaryotic host organism.

By "antisense" is meant a nucleic acid, regardless of length, that is complementary to a coding strand or mRNA of the invention. In some embodiments, the antisense molecule inhibits the expression of only one nucleic acid, and in other embodiments, the antisense molecule inhibits the expression of more than one nucleic acid. Desirably, the antisense nucleic acid decreases the expression or biological activity of a nucleic acid or protein of the invention by at least 20, 40, 50, 60, 70, 80, 90, 95, or 100%. An antisense molecule can be introduced, e.g., to an individual cell or to whole animals, for example, it may be introduced systemically via the bloodstream. Desirably, a region of the antisense nucleic acid or the entire antisense nucleic acid is at least 70, 80, 90, 95, 98, or 100% complementary to a coding sequence, regulatory region (5' or 3' untranslated region), or an mRNA of interest. Desirably, the region of complementarity includes at least 5, 10, 20, 30, 50, 75, 100, 200, 500, 1000, 2000, or 5000 nucleotides or includes all of the nucleotides in the antisense nucleic acid.

In some embodiments, the antisense molecule is less than 200, 150, 100, 75, 50, or 25 nucleotides in length. In other embodiments, the antisense molecule is less than 50,000; 10,000; 5,000; or 2,000 nucleotides in length. In certain embodiments, the antisense molecule is at least 200, 300, 500, 1000, or 5000 nucleotides in length. In some embodiments, the number of nucleotides in the antisense molecule is contained in one of the following ranges: 5-15 nucleotides, 16-20 nucleotides, 21-25 nucleotides, 26-35 nucleotides, 36-45 nucleotides, 46-60 nucleotides, 61-80 nucleotides, 81-100 nucleotides, 101-150 nucleotides, or 151-200 nucleotides, inclusive. In addition, the antisense molecule may contain a sequence that is less than a full-length sequence or may contain a full-length sequence.

The invention provides a number of targets that are useful for the development of drugs that specifically block the pathogenicity of a microbe, for example, *Pseudomonas aeruginosa* PA14. In addition, the methods of the invention provide a facile means to identify compounds that are safe for use in eukaryotic host organisms (i.e., compounds which do not adversely affect the normal development and physiology of the organism), and efficacious against pathogenic microbes (i.e., by suppressing the virulence of a pathogen). In addition, the methods of the invention provide a route for analyzing virtually any number of compounds for an anti-virulence effect with high-volume throughput, high sensitivity, and low complexity. The methods are also relatively inexpensive to perform and enable the analysis of small quantities of active substances found in either purified or crude extract form.

BRIEF DESCRIPTION OF THE FIGURES

FIGS. 11A-11E shows the nucleic acid sequences and amino acid sequences of PqsA-E, H, and L and mvfR, as well as the promoter region of the pqsA-E operon.

FIG. 12 is a table showing the percent relative concentration of extracellular compounds in culture supernatants of PA14 mutant strains versus the wild type PA14 strain. Cells were cultivated in LB medium for 11 hrs at 37° C. to a final $OD_{600}$=4. Data are averages of triplicate experiments ±SD. HHQ, 4-hydroxy-2-heptylquinoline; PQS, $Pseudomonas$ quinolone signal (3,4-dihydroxy-2-heptylquinoline); HNQ, 4-hydroxy-2-nonylquinoline; diHNQ, 3,4-dihydroxy-2-nonylquinoline; AA, anthranilic acid; NT, not tested; mvfR compl. is the mutant strain complemented with pDN18mvfR.

FIG. 13 is a table showing the concentration of PQS (μg/ml) and phzl gene expression in a lasR mutant culture and a 1:1 lasR mutant: mvfR mutant culture. Cultures were assayed at 8 hr sampling time, corresponding to $OD_{600}$ 4.3 to 4.5. *Ratios have been corrected by taking into account that the mixed culture contains 50% less lasR mutant cells than the lasR culture. mvfR mutant cells do not produce PQS. †The lasR mutant carries a phzABC-lacZ fusion. Data correspond to averages of triplicates±standard deviation; MU: Miller units.

FIG. 14 is a table showing the effect of HHQ addition on phzl gene expression in PA14 and lasR$^-$ cultures. Cultures were assayed at 8 hr, corresponding to $OD_{600}$ 4.3 to 4.5. The bacteria carry a phzABC-lacZ fusion. Data correspond to averages of triplicates±standard deviation; MU: Miller units.

DETAILED DESCRIPTION

Figure 1:
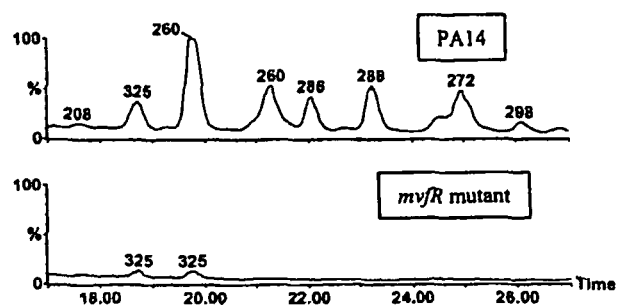
FIG. 1 shows LC/MS analysis of PA14 and mvfR mutant culture supernatants. MS chromatograms of PA14 (upper trace) and the mvfR mutant (lower trace). The numbers above the peaks represent the m/z values of the most intense ions. Intensities are normalized to the most abundant ion in the upper trace

In general, the present invention is based on our discovery that the pathogenic Pqs proteins mediate the biosynthesis of of extracellular signalling molecules involved in bacterial quorum sensing. Based on our results, the invention provides screening methods for identifying candidate compounds useful for the treatment, reduction, or prevention of pathogenic infections. Also disclosed are methods or treating, reducing, or preventing pathogenic infections, caused, for example, by $Pseudomonas$ $aeruginosa$.

Bacterial communities utilize 'Quorum Sensing' (QS) to coordinate their population behavior through the action of extracellular signal molecules, such as the N-acyl-L-homoserine lactones (AHLs). The versatile and ubiquitous opportunistic pathogen $Pseudomonas$ $aeruginosa$ is a well-studied model for AHL-mediated QS. This species also produces an intercellular signal distinct from AHLs, 3,4-dihydroxy-2-heptylquinoline (PQS), which belongs to a family of poorly characterized 4-hydroxy-2-alkylquinolines (HAQs) which are associated with antimicrobial activity.

Here we use LC/MS, genetics, and whole-genome expression to investigate the structure, biosynthesis, regulation, and activity of HAQs. We first demonstrate that the MvfR transcriptional regulator controls pqsA-E expression. Our results show that the pqsA-E operon encodes enzymes that direct the biosynthesis of five classes of HAQs, including molecules that function as antibiotics and cytochrome inhibitors and, significantly, as intercellular communication molecules. We have also found that anthranilic acid, the product of the PhnAB synthase, is the primary precursor of HAQs; and that the HAQ congener 4-hydroxy-2-heptylquinoline (HHQ) is the direct precursor of the PQS signaling molecule, which is itself a message molecule involved in cell-to-cell communication. While phnAB and pqsA-E are positively regulated by the virulence-associated transcription factor MvfR, which is also required for the expression of several QS-regulated genes, the conversion of HHQ to PQS is instead controlled by LasR. Our results further reveal that HHQ is itself both released from, and taken up by bacterial cells, where it is converted into PQS, which may subsequently function as a messenger molecule in a cell-to-cell communication pathway. HAQ signaling represents a potential target for the pharmacological intervention of $P.$ $aeruginosa$-mediated infections.

Screening Assays

The present invention provides screening methods to identify compounds useful (e.g., a peptide, polypeptide, synthetic organic molecule, naturally occurring organic molecule, nucleic acid molecule, or component thereof) for the treatment, prevention, or reduction of pathogenic infections. Using such agents as lead compounds, for example, the present screening methods also allow the identification of further novel, specific agents that function to treat, reduce, or prevent pathogenic infections. The method of screening may involve high-throughput techniques. A number of methods are available for carrying out such screening assays.

Figure 5:
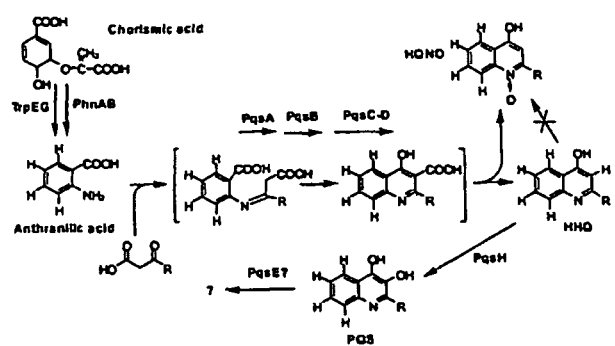
FIG. 5 is a schematic diagram showing the HAQ biosynthetic pathway in *P. aeruginosa*. The sequence of synthesis was determined by supplementing cultures of PA14 and various pqs/mvfR mutants with deuterium-labelled intermediates. Bracketed structures are hypothetical.

According to one approach, candidate compounds are added at varying concentrations to the culture medium of pathogenic cells (any pathogenic cell, such as those that infect mammals (e.g., *Pseudomonas aeruginosa* such as PA14 or PAO1) or plants) after which the production of an HAQ molecule, HHQ molecule, or a derivative or precursor thereof is measured using any standard method known in the art or described herein. For example, the production of an HAQ molecule may be determined by measuring the antimicrobial activity of the HAQ molecule. Exemplary HAQ molecules, HHQ molecules, or precursors or derivatives thereof are provided in FIG. 5 and FIG. 2.

Alternatively, the screening methods of the invention may be used to identify candidate compounds to decrease the production of an HAQ molecule or an HHQ molecule (thereby decreasing the production of PQS, in turn reducing the virulence of a pathogenic cell) by their ability to reduce, treat, or prevent a pathogenic infection. Such reduction is desirably at least 10%, 20%, 30%, 40%, 50%, 60%, 70%, 80%, 90%, 95%, or 100% relative to an untreated control. The virulence of a pathogenic cell may be measured using the cell-based methods or in vivo methods herein.

Alternatively, the screening method may involve contacting a population of pathogenic cells with a candidate compound, culturing the population of cells for a predetermined amount of time, and collecting the supernatant from the population of cells. A useful candidate compound would inhibit any step of the HHQ biosynthesis pathway shown in FIG. 5 or FIG. 2, such that the production of HHQ would be reduced. The collected supernatant is next placed on a second population of cells expressing a PqsH protein (or a chemical derivative thereof) after which the production of PQS from this second population is measured by any method known in the art. If the candidate compound reduces the production of PQS in this population of cells relative to a control population that has been contacted with supernatant collected from pathogenic cells cultured in the absence of a candidate compound, this candidate compound is identified as being useful for treating, preventing, or reducing a pathogenic infection by virtue of its ability to interfere with the HHQ biosynthesis pathway. The PqsH protein used in this assay may be encoded by a nucleic acid of SEQ ID NO: 6 or by a nucleic acid molecule that binds under stringent conditions to SEQ ID NO: 6 or a sequence complementary thereto. Alternatively, the PqsH protein is substantially identical to the amino acid sequence of SEQ ID NO: 13. Pathogenic cells may either endogenously express PqsH or may alternatively be genetically engineered by any standard technique known in the art (e.g., transfection and viral infection) to overexpress PqsH. The effect of a candidate compound on the production of PQS may be tested by radioactive and non-radiaoctive binding assays, competition assays, and signaling assays.

Ultimately, the screening assay of the invention may be carried out, for example, in a cell-free system. If desired, one of the Pqs proteins, HAQ molecules, HHQ molecules, or the candidate compound may be immobilized on a support as described above or may have a detectable group.

Alternatively, or in addition, candidate compounds may be screened for those which specifically bind to and thereby reduce HAQ or HHQ activity or levels. The efficacy of such a candidate compound is dependent upon its ability to interact with such molecules. Such an interaction can be readily assayed using any number of standard binding techniques and functional assays (e.g., Ausubel et al., *Current Protocols in Molecular Biology*, 2004, John Wiley and Sons). For example, a candidate compound may be tested in vitro for interaction and binding with an HAQ molecule or HHQ molecule or derivative or precursor thereof and its ability to reduce HAQ or HHQ activity or levels may be assayed by any standard assays (e.g., those described herein).

In one particular example, a candidate compound that binds to HHQ may be identified using a chromatography-based technique. For example, an HHQ molecule may be produced by standard techniques (e.g., those described above) and may be immobilized on a column. Alternatively, the naturally-occurring HHQ molecule may be immobilized on a column. A solution of candidate compounds is then passed through the column, and a compound specific for HHQ is identified on the basis of its ability to bind to HHQ and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography).

Alternatively, the invention also provides a method of identifying a candidate compound by contacting a candidate compound, a Pqs protein (e.g., pqsA, pqsB, pqsC, pqsD, pqsE, pqsH, and pqsL protein), and an HAQ or HHQ molecule capable of binding the Pqs protein under conditions that allow binding. If HHQ is used in this method instead of an HAQ molecule, a PqsH protein is used. Binding of this Pqs protein to the HAQ molecule or HHQ molecule is next measured such that a decrease in binding effected by the candidate compound identifies a candidate compound useful for treating, reducing, or preventing a pathogenic infection. The Pqs protein may contain an amino acid sequence substantially identical to any one of SEQ ID NOs: 8-14, or may alternatively be encoded by a nucleic acid molecule that is substantially identical to or that hybridizes under stringent conditions to any one of SEQ ID NOs:1-7.

Alternatively, the invention also provides a method of identifying a candidate compound by contacting a candidate compound, an MvfR protein, a nucleic acid sequence substantially identical to the nucleic acid of SEQ ID NO:15 or with a nucleic acid molecule that binds under stringent conditions to SEQ ID NO:15 or a sequence complementary thereto or fragment thereof (e.g. the lysR-box sequence). Binding of MvfR to this nucleic acid is next measured such that a decrease in binding effected by the candidate compound identifies a candidate compound useful for treating, reducing, or preventing a pathogenic infection. The MvfR protein may contain an amino acid sequence substantially identical to any one of SEQ ID NO:17, or may alternatively be encoded by a nucleic acid molecule that is substantially identical to or that hybridizes under stringent conditions to any one of SEQ ID NO:16.

Alternatively, the invention also provides a method of identifying a candidate compound by contacting a candidate compound, a cell (for example, a cell such as a mutant pqs strain (e.g., a pqsA mutant strain) of a pathogenic cell (any pathogenic cell, such as those that infect mammals (e.g., *Pseudomonas aeruginosa* such as PA14 or PAO1) or plants)) containing a pqs-reporter (e.g., a pqsA-LacZ reporter), and a PQS molecule. The output level of the reporter construct is next measured such that a decrease in output effected by the candidate compound identifies a candidate compound useful for treating, reducing, or preventing a pathogenic infection.

Alternatively, the invention also provides a method of identifying a candidate compound by contacting a candidate compound, a nucleic acid of SEQ ID NO:15 or by a nucleic acid molecule that binds under stringent conditions to SEQ ID NO:15 or a sequence complementary thereto or fragment thereof (e.g., a fragment containing a lysR-box). The binding of this nucleic acid to the candidate compound identifies a candidate compound useful for treating, reducing, or preventing a pathogenic infection.

Screening for new inhibitors and optimization of lead compounds may be assessed, for example, by assessing their ability to function as anti-pathogenic agents (e.g., as described herein). Compounds isolated by this approach may also be used, for example, as therapeutics to treat, reduce, or prevent pathogenic infections. Compounds which are identified as binding to HHQ or HAQ with an affinity constant less than or equal to 10 mM are considered particularly useful in the invention.

Ultimately, the anti-pathogenic efficacy of any of the candidate compounds identified by the present screening methods may be tested using any of the pathogenicity models described herein or known in the art.

Potential therapeutic agents include organic molecules, peptides, peptide mimetics, polypeptides, and antibodies. Potential anti-pathogenic agents also include small molecules that bind to and occupy the binding site of Pqs polypeptides thereby preventing binding to cellular binding molecules, such that normal biological activity is reduced, in turn reducing HHQ and PQS production and pathogenic virulence. Other potential anti-pathogenic agents may also include antisense molecules.

Test Compounds and Extracts

In general, compounds capable of treating, reducing, or preventing pathogenic infections are identified from large libraries of both natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are also commercially available. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-hypertensive activity should be employed whenever possible.

When a crude extract is found to have an anti-pathogenic activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having anti-pathogenic activity. Methods of fractionation and purification of such heterogenous extracts are known in the art. If desired, compounds shown to be useful agents for the treatment of pain are chemically modified according to methods known in the art.

Results

HAQ Identification: mvfR is Required for the Production of Five Distinct Series of HAQs from the Common Precursor Anthranilic Acid Calfee et al. (*Proc. Natl. Acad. Sci. USA* 98, 11633-11637, 2001) recently reported that $^{14}$C-labelled AA is incorporated into PQS, but that this PQS represents only 12% of the newly synthesized compounds, indicating that the ethyl acetate extract contains additional AA-derived molecules. Because HHQ biosynthesis proceeds from the coupling of AA and an α-keto fatty acid (Ritter et al., *Eur. J. Biochem.* 18, 391-400, 1971), we hypothesized that these unidentified AA-derived molecules might correspond to HAQs related to PQS and HHQ.

Figure 8:
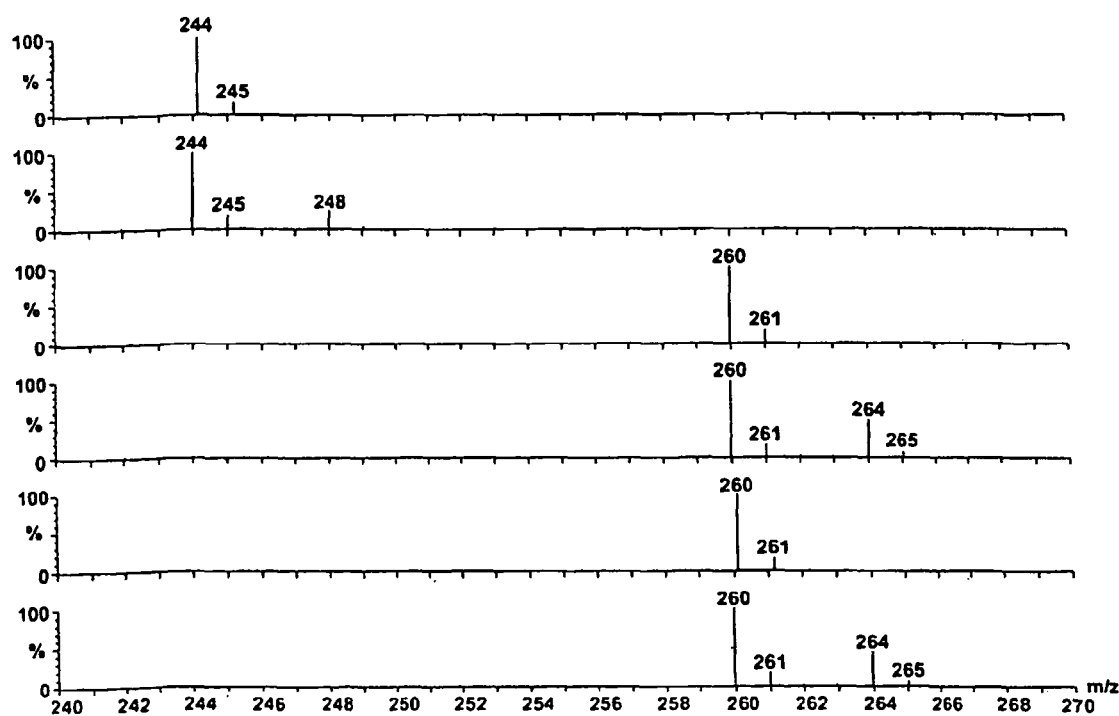
FIG. 8. shows the MS spectra of HHQ, PQS and HQNO in PA14 culture supernatant grown in the presence or absence of 3,4,5,6-tetradeutero-anthranilic acid. The six traces from the top to the bottom of figure respectively correspond to (1) unlabeled HHQ; (2) deuterated HHQ; (3) unlabeled PQS; (4) deuterated PQS; and (5) unlabeled HQNQ; and (6) deuterated HQNQ.

To this end, we fed AA or deuterated AA (AA-$d_4$) to PA14 cultures, and analyzed the culture supernatants using LC/MS (Lépine et al., *Biochim. Biophys. Acta* 1622, 36-40, 2003). The resulting chromatograms exhibit several peaks in the vicinity of PQS and the mass spectra of these compounds all show the addition of 4 Da in the cultures fed AA-$d_4$, demonstrating that AA is their common precursor (FIG. 8). Since we have previously shown that PQS production is abrogated in an mvfR mutant (Cao et al., *Proc Natl. Acad. Sci. USA* 98, 14613-8, 2001), we investigated the synthesis of these compounds in this mutant. FIG. 1 shows that all the deuterium-labeled peaks are absent from the mvfR mutant culture supernatant; with the only residual peaks found at HAQ retention times corresponding to two conformers of the siderophore pyochelin (Rinehart et al., *J. Org. Chem.* 60, 2786-2791, 1995), which give M+H ions at m/z 325 and are structurally unrelated to HAQs.

Figure 2:
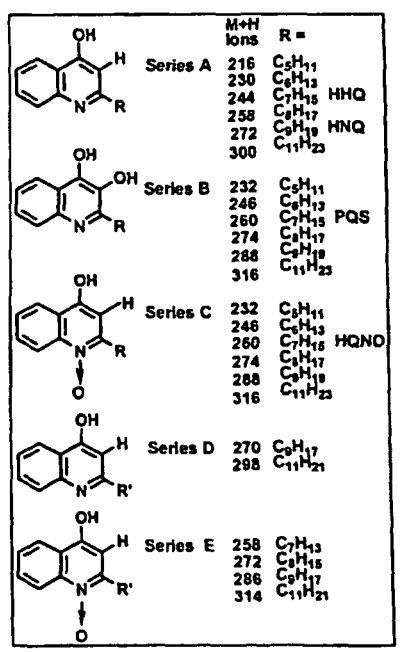
FIG. 2 shows chemical structures of five distinct series of HAQ compounds isolated from the PA14 culture supernatant. Detailed MS analysis of the peaks in FIG. 1. R, alkyl side chain length.

The mass spectra of these labeled peaks show that they correspond to five distinct series of HAQs (FIG. 2). All these congeners share the common basic 4-hydroxyquinoline structure of series A with an additional hydroxyl at the 3-position, as in series B, or with an N-oxide group as in series C and E. Within each series, the 2-position alkyl chain varies in length. Also, the series D and E alkyl side chain is unsaturated. The most abundant congeners contain an odd carbon number alkyl chain, with seven or nine carbons preponderant.

The HAQ congeners include both previously identified and novel compounds. The $C_7$ (HHQ) and $C_9$ (HNQ) congeners are shown in FIG. 2 (also see Wells, *J. Biol. Chem.* 196, 331-340, 1952), while the structures of the other series A congeners were later determined using GC/MS (Taylor et al., *J. Chromatogr. B Biomed. Appl.* 664, 458-62, 1995). In contrast, the only reported series B congener is 3,4-dihydroxy-2-heptylquinoline, first isolated in 1959 (Takeda, *Hakko Koyaku Zasshi* 37, 59-63, 1959), and later fully characterized and named PQS (Pesci et al., *Proc. Natl. Acad. Sci. USA* 96, 11229-11234, 1999). For series C, the $C_7$, $C_9$, $C_8$ and $C_{11}$ congeners have been reported (Cornforth et al., *Biochem. J.* 63, 124-130, 1956; Luckner et al., *Tetrahedron Letters* 12, 741-744, 1965), and are further discussed below, while the series E and the series B PQS congeners are unique to this study. The novelty of many of our HAQs, such as the series B molecules, and the series C and E congeners, which have polar N-oxide functions, is because previous studies employed derivatization prior to GC/MS injection (Machan et al., *J. Antimicrob. Chemother.* 30, 615-623, 1992; Taylor et al., *J. Chromatogr. B Biomed. Appl.* 664, 458-62, 1995). Positive electrospray ionization mass spectrometry is better suited than GC/electron impact-MS for the detection of such relatively basic compounds.

Figure 3:
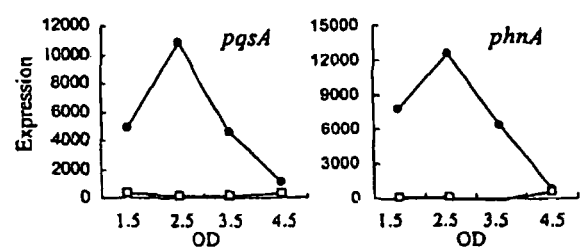
FIG. 3 shows the expression profiles of pqsA and phnA in PA14 versus the mvfR mutant, using the GeneChip® *P. aeruginosa* array. (●), PA14; (□), the mvfR mutant. Signal intensity values calculated by dCHIP software. OD, optical density at 600 nm of the cultures when harvested.
Figure 4:
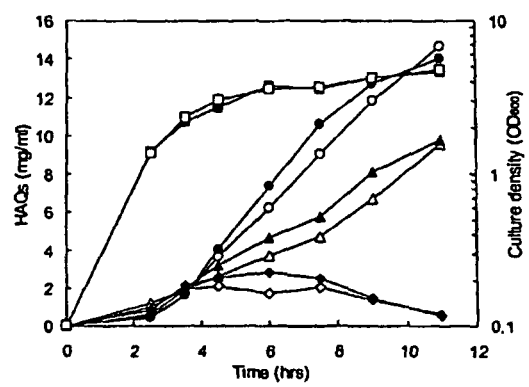
FIG. 4 shows HAQ production kinetics in PA14 versus the isogenic pqsE mutant. Bacteria were grown in LB at 37° C. and their extracellular HAQ concentrations were analyzed by MS at regular time intervals. Solid symbols, PA14; Open symbols, pqsE mutant; (●,□), Optical density of the culture [$OD_{600}$]; (●,○), PQS; (▲,△), HQNO; (♦,◇), HHQ.
Figure 9:
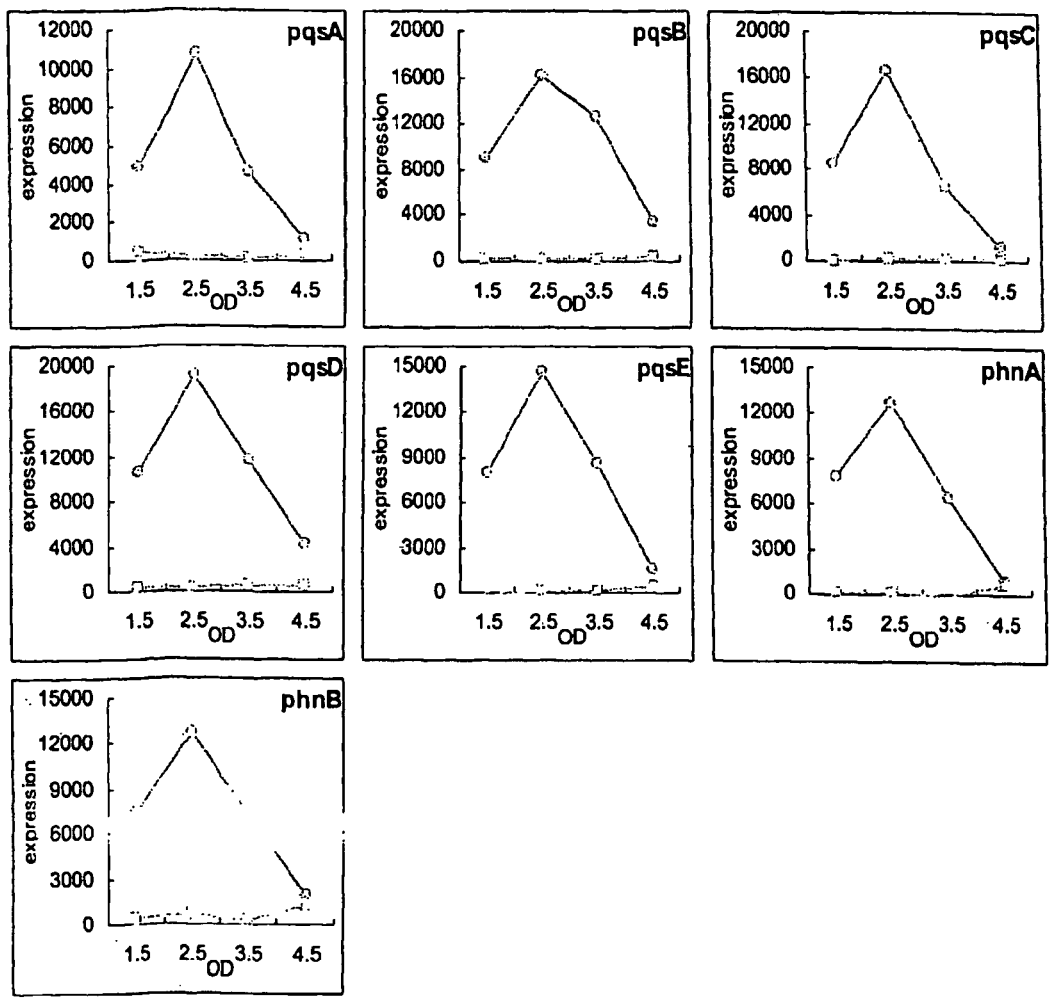
FIG. 9 shows expression of the pqsABCDE and phnAB genes in whole-genome transcriptome profiles of PA14 and the mvfR mutant using the $P.$ $aeruginosa$ GeneChip® array. (●), PA14; (□), mvfR mutant. OD, optical density of the harvested culture samples at 600 nm. Signal intensity values were calculated using dCHIP.

HAQ Regulation: MvfR Controls the Expression of the phnAB and pqsA-E Operons, Which are Required for HAQ Synthesis That MvfR regulates phnAB expression (Cao et al., *Proc. Natl. Acad. Sci. USA* 98, 14613-8, 2001) suggests that it might also direct HAQ biosynthesis by regulating genes that encode anabolic pathway enzymes. As part of a project to identify MvfR-regulated genes, we carried out a transcriptome comparative analysis between PA14 and its isogenic mvfR mutant at set time points during a growth time-course, using the Affymetrix *P. aeruginosa* GeneChip® oligonucleotide array. The expression profiles of the five genes just upstream from the anthranilate synthase phnAB operon tightly cluster with phnAB expression (FIG. 3 and FIG. 9), suggesting they are co-regulated. FIG. 4 shows that the expression patterns of these seven genes correlate with the kinetic rates of HAQ production, which are maximal at the end of exponential/early stationary phase (i.e., $OD_{600}$ 2.5) (Lépine et al., *Biochim. Biophys. Acta* 1622, 36-40, 2003). Since phnAB expression is under the control of MvfR (Cao et al., *Proc. Natl. Acad. Sci. USA* 98, 14613-8, 2001), it is not surprising that the transcription of these seven genes is almost completely abolished in the mvfR mutant (FIG. 3 and FIG. 9).

FIG. 12 shows that knockout inactivation of pqsA or pqsB results in the complete elimination of HAQ production and the striking accumulation of AA in culture supernatants. AA likely accumulates because these mutants fail to consume AA for HAQ synthesis, further supporting AA as the HAQ precursor. In contrast, a pqsE mutant produces wild-type levels of HAQ and AA (FIG. 4), in agreement with the observation that pqsE inactivation does not affect PQS production (Gallagher et al., *J Bacteriol* 184, 6472-80, 2002). Genetic complementation suggests that pqsABCDE is a single operon (Gallagher et al., *J Bacteriol* 184, 6472-80, 2002). Our expression profiling data corroborate the LC/MS results and further indicate that MvfR controls the transcription of the co-regulated pqsABCDE and phnAB operons.

Figure 10:
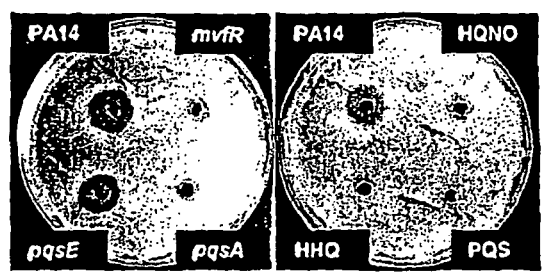
FIG. 10 shows an assay of HAQ antimicrobial activity. $Bacillus$ $subtilis$ growth on well plates was scored for inhibition by culture extracts of PA14 and the mvfR, pqsA, and pqsE mutant strains (left plate), and by purified PQS, HHQ and HQNO, versus PA14 extract (right plate).

HAQ Activity: MvfR Regulates HQNO Antimicrobial Activity Against Gram-Positive Bacteria Fluorescent pseudomonads, and perhaps just *P. aeruginosa*, are the only microorganisms identified to produce HAQs (Budzikiewicz, *FEMS Microbiol. Rev.* 104, 209-228, 1993; Lépine et al., *Biochim. Biophys. Acta* 1622, 36-40, 2003). Although their biological functions are unknown, many HAQs were initially isolated as antibiotics (Hays et al., *J. Biol. Chem.* 159, 725-750, 1945; Wells, *J. Biol. Chem.* 196, 331-340, 1952). We assayed the antimicrobial activity of total organic extracts from PA14 and mvfR, pqsA, and pqsE mutant strains, and purified PQS, HHQ and HQNO, against the Gram-positive species *Staphylococcus aureus* and *Bacillus subtilis*. PA14 and pqsE⁻ extracts clearly inhibit both species, while the pqsA⁻ and mvfR⁻ extracts have low or no antibacterial activity (FIG. 10). Thus, MvfR regulates the production of antibiotics that can function in niche competition against other bacteria. Because the pqsE mutant and PA14 produce roughly the same levels of antimicrobial activity, these antibiotic compounds are probably HAQs, instead of other non-polar compounds whose synthesis is under PQS control.

While it has been known for many decades that *P. aeruginosa* produces low molecular weight antibiotics, later found to be HAQs (Bouchard, *Compt. rend Acad. Sci.* 108, 713-714, 1889; Hays et al., *J. Biol. Chem.* 159, 725-750, 1945), these compounds have been little characterized. Although the HAQ N-oxides ($C_7$-, $C_9$-, and $C_{11}$-) were originally isolated as streptomycin and dihydrostreptomycin antagonists (Sureau et al., *Ann. Inst. Pasteur Paris* 75, 169-171, 1948; Lightbown, *J. Gen. Microbiol.* 11, 477-492, 1954; Cornforth et al., *Biochem. J.* 63, 124-130, 1956), their mode of action remains unknown. We confirm here the specific antibacterial activity of HQNO (FIG. 10), in agreement with Machan et al., *J. Antimicrob Chemother* 30, 615-623, 1992. This $C_7$ congener, which is a widely used cytochrome inhibitor (Lightbown et al., *Biochem. J.* 63, 130-137, 1956), and also inhibits $Na^+$-translocating NADH-quinone oxidoreductases (Häse et al., *Microbiol Mol Biol Rev* 65, 353-70 2001), may therefore function in nature as a virulence factor.

HAQ Biosynthetic Machinery: PQS is not a Product of the mvfR-Regulated Synthetic Pathway The similarity of the HAQ structures, along with their co-labeling from deuterated AA, suggests they are produced via a common biosynthetic pathway. To this end, we added various known or putative labeled HAQ precursors and derivatives to cultures of PA14 or isogenic pqs and mvfR mutants, to generate the pathway in FIG. 5. Addition of HHQ-$d_4$ to PA14 cultures results in overproduction and labeling of PQS, indicating that HHQ is an intermediate in PQS biosynthesis. Also, as no overproduction or labeling of HQNO is detected, HHQ is not a precursor of HQNO. By analogy, the series A compounds, which include HHQ, are the probable precursors of the corresponding series B compounds, but not the other series. To examine whether PQS is an intermediate in HAQ biosynthesis, PQS-$d_4$ was added to PA14 cultures. Since none of the chromatographic peaks are labeled, PQS must be an end-product in HAQ biosynthesis, or at least is not substantially converted into an extracellular compound. Also, as all HHQ-$d_4$ added to pqs/mvfR mutant cultures is completely converted into PQS, MvfR does not control the final step(s) of PQS synthesis.

We were unable to determine the precise origin(s) of the N-oxides (series C and E). Nevertheless, these HAQs clearly belong to the above pathway since AA-$d_4$ addition results in labeled N-oxides, and they are absent in mutants that fail to synthesize HAQs; however, as proposed in FIG. 5, N-oxides are probably not synthesized downstream of HHQ or PQS, because cultures supplemented with these deuterated compounds do not produce the corresponding labeled N-oxides. The N-oxides do not appear to be HAQ precursors, via simple reduction of their N-oxide function, since adding HQNO-$d_4$ to PA14 cultures neither results in decreased labeled N-oxide concentrations in the culture medium, nor labeling of any HAQ congeners. Because HQNO is a cytochrome inhibitor and has antimicrobial activity, it seems likely that it is actively exported, which would mask its role in HAQ biosynthesis in our assay. Nevertheless, N-oxides are probably the end-products of a branch pathway that is not under mvfR regulation. Indeed, we have shown that series A, B and D congener concentrations decrease in culture supernatants after peaking, whereas the concentrations of the N-oxides (series C and E) remain stable (Lépine et al., *Biochim. Biophys. Acta* 1622, 36-40, 2003).

Overexpression of mvfR results in the excessive accumulation of series A compounds (the series B precursors; HHQ and HNQ in FIG. 12) in the supernatant, but leaves series B, C and E (PQS congeners and N-oxides) concentrations largely unaffected (FIG. 12), indicating that the series A (and D) congeners are end-products of the mvfR-regulated synthetic pathway. These data also support the conclusions that MvfR does not directly control PQS production, and that the branch pathways leading to series B, C, and E are saturated when the mvfR-regulated pathway is over-activated. Similarly, that a lasR mutant produces significant amounts of HAQs (FIG. 12), with the over-accumulation of series A congeners (the PQS analogue precursors), suggests that the QS transcriptional regulator LasR controls the series A to series B conversion. This step is likely mediated by the PqsH-encoded FAD-dependent monooxygenase, a QS-controlled gene that is required for PQS synthesis (Gallagher et al., *J. Bacteriol.* 184, 6472-80, 2002) and is under LasR regulation (Whiteley et al., *Proc. Natl. Acad. Sci. USA* 96, 13904-1890, 1999).

Collectively, our results show that the series A compounds are the end-product of the mvfR-controlled biosynthetic pathway, and are subsequently converted into the series B PQS analogues via a lasR-dependent pathway, likely via the PqsH enzyme, which is not under MvfR regulation. These results suggest that the final synthesis of the active PQS signal is highly regulated and under additional controls beyond those of the primary HAQ pathway.

HHQ, the PQS Precursor, Functions in Cell-To-Cell Communication

PQS is an extracellular signal that participates in the QS circuitry. Several observations suggest that HHQ also functions as an intercellular messenger: (a) it is released by bacteria; (b) its concentration rises during exponential growth phase, and then decreases during PQS production (FIG. 4); (c) it is taken up by bacterial cells, converted into PQS, and then released into the extracellular milieu, as shown in the labeling experiments; and (d) its synthetic pathway, via PqsA-D is distinct and under different regulation than that of HHQ-to-PQS conversion, via PqsH. These results collectively suggest the model depicted in FIG. 6, in which HHQ is released by cells and acts as a messenger that is subsequently converted into the PQS signal by the cells that take it up. To test this hypothesis, we compared PQS production in a lasR mutant culture, versus that of a mixed culture of lasR and mvfR mutant cells. FIG. 12 shows that the lasR mutant produces low levels of PQS and accumulates high concentrations of HHQ due to its low PqsH activity; and the mvfR mutant produces no PQS, as it is unable to synthesize the HHQ precursor. Thus, using these two mutants, one able to produce HHQ but unable to process it into PQS, and the other unable to produce HHQ, but able to convert it into PQS, should allow us to verify whether a *P. aeruginosa* cell can produce PQS using HHQ produced by another cell. Indeed, FIG. 13 shows that when the two mutants are grown together, PQS concentration is up to five times higher than if the cells fail to exchange the signaling information.

phzl operon expression, which is required for the synthesis of pyocyanin, depends on both PQS signaling and pqsE expression. Therefore, to determine whether the PQS that is produced and released by mvfR⁻ cells, when they are co-cultured with the lasR⁻ cells, is biologically active in adjacent cells, we introduced a phzABC-lacZ reporter fusion into the lasR⁻ mutant, where pqsE is expressed, and compared the β-galactosidase activity with and without co-cultivation with mvfR mutant cells. FIG. 13 shows that phzl operon expression is indeed upregulated in the presence of mvfR⁻ cells, indicating that the PQS produced by mvfR mutant cells is taken up by the lasR⁻ bacteria, where it activates the phzl operon. Accordingly, the mixed culture, but not the cultures of either mutant alone, also generates pyocyanin (FIG. 7). The lasR mutant is responsible for this pyocyanin production, because while the mvfR mutant "sees" PQS, it fails to express pqsE. Indeed, no β-galactosidase induction is obtained in a cocultivation experiment where the phzABC-lacZ reporter is carried by the mvfR⁻ versus the lasR⁻ cells, Although mutants were used for this demonstration, the "conversational" pathway presented in FIG. 6 may occur in wild-type cell cultures, since PA14 cells similarly perform HHQ release, uptake, and PQS conversion.

To determine whether HHQ is itself involved in signal gene regulation, independently from PQS activity, or whether it functions solely as a PQS precursor, we asked whether exogenous HHQ can stimulate the activity of a phzABC-lacZ reporter carried by wild-type PA14 cells, and by lasR⁻ mutant cells. While HHQ addition to the culture medium has no effect on this activity in the lasR mutant, it induces significant and consistent levels of β-galactosidase activity in the wild-type strain (FIG. 14). Similar results are also observed with an hcnA'-lacZ fusion. These findings demonstrate that HHQ can induce the expression of genes that are also activated by PQS (Gallagher et al., *J Bacteriol* 184, 6472-80, 2002), and this induction appears to require HHQ conversion into PQS, since no induction is found in cells that cannot carry out this conversion. Thus, HHQ does not itself function as a signal in our assay, independent of PQS activity, but instead is able to act as a messenger molecule that is converted into PQS by cells other than those that produce it.

Figure 6:
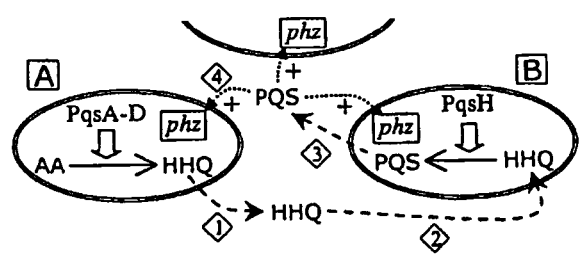
FIG. 6 is a schematic diagram showing HHQ/PQS cell-to-cell communication model. (1) HHQ is synthesized and released by bacterial cells; (2) extracellular HHQ is taken up by adjacent bacteria and converted into PQS, possibly in the periplasm; (3) PQS is released to act as a signaling molecule for other cells; and (4) PQS activates target gene expression, such as the phzl operon. Note that both HHQ availability and PqsH activity determine the final PQS concentration. In the experimental paradigm used to test the model (see text), cell [A] and cell [B] were an mvfR mutant and a lasR mutant, respectively. In the case of a wild type population, both the [A] and [B] cells are producing HHQ and PQS.
Figure 7:
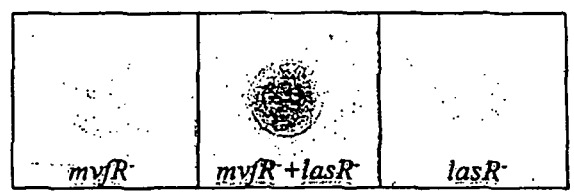
FIG. 7 shows Pyocyanin production in a mixed-mutant culture illustrates the HAQ cell-to-cell communication pathway. Culture suspensions of the mvfR mutant, the lasR mutant, or a 1:1 mixture of both, were spotted onto an LB plate and incubated for 18 hrs at 37° C. Only the mixed culture produces detectable amounts of pyocyanin, presumably from the lasR$^-$ cells, as mvfR$^-$ cells are deficient for phzl operon expression. This result demonstrates that HHQ, produced by the lasR$^-$ cells, is released and taken up by the mvfR$^-$ cells and converted into PQS. This PQS signal is then released by the mvfR$^-$ cells and taken up by the lasR$^-$ cells, where it signals phzl expression and pyocyanin production.

Reduced Pathenogenicity of pqs Operon Mutants mvfR and pqsB mutants display reduced pathogenicity in plants, nematodes, insects, and mice (see references Wells, *J. Biol. Chem.* 196, 331-340, 1952; Rahme et al., *Proc. Natl. Acad. Sci. USA* 94, 13245-13250, 1997; 47, 48). When using the burn mouse model for mammalian pathogenicity assessment, PA14 induces a mortality rate of near 100 %, whereas its isogenic mvfR mutant gives only about 35 % mortality (Cao et al., *Proc Natl. Acad. Sci. USA* 98, 14613-8, 2001). Accordingly, we found here the pqsA and pqsE mutants also displayed attenuated mice virulence, with mortality rates of 40%±3 and 38%±12, respectively, thus confirming the importance of these mvfR-regulated genes in mammalian pathogenesis. This reduced pathogenicity presumably results from the down-regulation of QS-controlled virulence factors that require PQS synthesis (see references: McKnight et al., *J. Bacteriol.* 182, 2702-2708, 2000; Lépine et al., *Biochim. Biophys. Acta* 1622, 36-40, 2003), and/or a reduction of pqsE expression (Rahme et al., *Science* 268, 1899-1902, 1995). The pqsE mutant, which produces wild-type HAQ levels, also exhibits attenuated virulence (FIG. 4 and Wells, *J. Biol. Chem.* 196, 331-340, 1952); therefore PQS might not be directly relevant to pathogenicity.

pqsE does not Participate in Extracellular HAQ Synthesis, but is Essential for the QS Regulatory Activity of mvfR Whereas pqsA or pqsB inactivation abolish HAQ production, a pqsE mutant produces essentially normal HAQ levels (FIG. 12), and HAQ-related antibiotic activity (FIG. 6). Indeed, a detailed kinetic analysis shows that pqsE inactivation has no effect on HAQ production (FIG. 4). In contrast, both its pyocyanin production and mouse pathogenicity are as attenuated as seen with the mvfR or other pqs mutants. Moreover, PQS addition to cultures of any pqs or mvfR mutants, or induction of PQS synthesis by HHQ addition, failed to induce pyocyanin production, potentially because of the lack of pqsE expression in these mutants. This was unexpected since the QS regulatory activity of mvfR was hypothesized to reflect the lack of PQS synthesis, suggesting that the presence or production of PQS is insufficient to activate pyocyanin synthesis, and perhaps other mvfR-controlled pathogenicity-related activities, whereas pqsE expression is essential. Supporting this notion, mvfR overexpression gave excessive pyocyanin accumulation (FIG. 12). BLAST analysis and genomic context suggest that pqsE encodes an enzyme, perhaps a hydrolase, which converts PQS congeners into intracellularly active derivatives. Such compounds would not be detected by our assay, which was aimed at extracellular compounds. Loss of these compounds might underlie the reduced pathogenicity of a pqsE mutant.

Thus, using LC/MS and DNA microarray analyses, we have determined that the transcriptional regulator MvfR, originally identified via its requirement for full *P. aeruginosa* broad-host virulence, regulates the expression of pqsABCDE and phnAB, which encode enzymes involved in the synthesis of five distinct families of structurally related HAQ congeners. By adding labeled HAQ precursors to bacterial cultures, we have found that AA, mostly the product of the PhnAB synthase, is the precursor of all HAQs, and have therefore established the sequence of their synthesis. Significantly, we show that PQS synthesis requires an activity whose regulation depends on LasR, versus MvfR. Our results also revealed that one HAQ, HHQ, is the precursor of the PQS signaling molecule, and is itself both released from and taken up by bacteria, implicating it as an intercellular message molecule. These results provide insights into the structure, biosynthesis, regulation, and function of HAQs, and have allowed us to uncover a 'conversational' cell-to-cell communication pathway used by *P. aeruginosa*.

At least two branch pathways appear to have evolved from an ancestral synthetic HAQ pathway—one leading to the production of the antibacterial and cytochrome inhibitor N-oxide derivatives, and the second leading to PQS signaling congeners. Many HAQs have been previously identified as *P. aeruginosa* secondary metabolites (Budzikiewicz, *FEMS Microbiol. Rev.* 104, 209-228, 1993; Leisinger et al., *Microbiol Rev* 43, 422-42, 1979). We have confirmed that a number of these compounds have Gram-positive antimicrobial activity, and have attributed some of this activity to HQNO, the most abundant HAQ. Interestingly, this activity has been associated with the clearance of *S. aureus* lung colonization by *P. aeruginosa* (Machan et al., *J. Antimicrob Chemother* 30, 615-623, 1992). HHQ is found in cystic fibrosis (CF) lung exudates (Machan et al., *J. Antimicrob. Chemother.* 30, 615-623, 1992) and PQS occurs in the sputum and bronchoalveolar lavage fluid of CF lungs (Collier et al., *FEMS Microbiol. Lett.* 215, 41-6, 2002), indicating that HAQs are produced in vivo. Guina et al. have reported that *P. aeruginosa* isolates from CF patients produce more PQS than isolates from other diseases, suggesting that the PQS pathway could be upregulated in CF strains (Guina et al., *Proc. Natl. Acad. Sci. USA* 100, 2771-2776, 2003). Thus, *P. aeruginosa*, when colonizing novel infectious niches, may increase HAQ production to inhibit the growth of competing microorganisms.

Our study provides novel insights into PQS signaling, which functions in the expression of QS-regulated genes. Our results demonstrate that this system acts via at least two distinct extracellular molecules: PQS, and its precursor, HHQ. As illustrated in FIG. 6, this pathway can be viewed as 'conversational' cell-to-cell communication, since an HHQ molecule released by a cell in a population is taken up by another cell and converted into PQS, where it is then released into the extracellular milieu, to signal cells in the population. This signaling is not artifactual and that HHQ and PQS could mean different things to cells in a population, even if their ultimate signaling mechanisms are the same. For instance, their concentrations peak at different growth stages; their production is under different regulation (MvfR for HHQ, LasR for PQS); and they are likely produced in different cellular compartments. Indeed, the PSORT program, predicts that the PqsH monoxygenase, which probably mediates the hydroxylation of HHQ into PQS, is localized to the periplasmic space. This suggests that the HHQ that is converted to PQS typically has an extracellular versus intracellular origin, and engenders the question of whether the intracellular HHQ is destined to serve as the PQS precursor.

Cells in a bacterial community need to tell each other about their different properties, including their density, growth state, and production levels of extracellular compounds, such as antibiotics and virulence factors, in order to coordinate their activity. Presumably, different signals are required to convey this different information, and *P. aeruginosa* populations likely employ panoply of extracellular molecules. For instance, although HHQ is the precursor of PQS, these two molecules could convey different information: HHQ reflects the extracellular levels of HAQ including antimicrobial and cytochrome inhibitory functions, and indicates the level of MvfR activity; while PQS reflects LasR activity levels and the status of the AHL-based QS system in population growth regulation. Also, that HAQ and PQS levels peak at different times suggests that PQS-mediated signaling reflects HAQ levels at one growth stage, and PQS levels at another.

Finally, HHQ and PQS analogues are largely cell-associated (Lépine et al., *Biochim. Biophys. Acta* 1622, 36-40, 2003), suggesting the possibility that HAQ-based intercellular communication is mediated through cell-to-cell contact. Such contact and intercellular communication may be particularly important in chronic *P. aeruginosa* infections, including those of the lungs of CF patients, as it is beneficial for bacteria to regulate their populations in such niches. Significantly, both HHQ and PQS are produced in the lungs of CF individuals (see references: Machan et al., *J. Antimicrob. Chemother.* 30, 615-623, 1992; Collier et al., *FEMS Microbiol. Lett.* 215, 41-6, 2002), suggesting that these molecules represent a pharmacological target for treating the debilitating *P. aeruginosa* infections common to CF patients.

PQS is Required for the Activation of pqsA-E Operon

Figure 15:
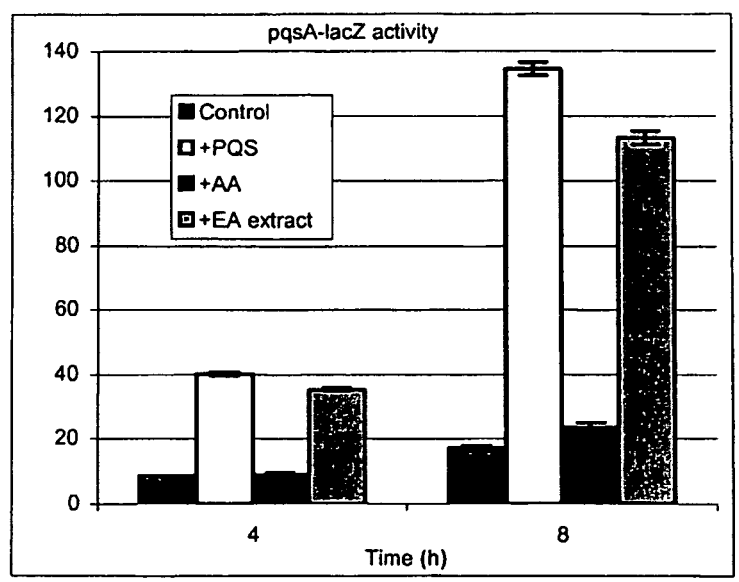
FIG. 15 shows PqsA-lacZ induction by PQS, anthranilic acid, and cell supernatant extract Compounds were added at the onset of culture at 10 mg/L final concentration. Activity is reported as Miller units (MU), corrected for the OD of the cultures at 600 nm.

To demonstrate that PQS indeed is an inducer, pqsA mutant cultures carrying the pqsA-lacZ reporter were exposed to PQS, anthranilic acid (AA), and complete supernatant extract (used in FIG. 8), and LacZ activity was measured. FIG. 15 demonstrates that PQS activates pqsA transcription in the mutant background (pqsA⁻), in the absence of HAQ production. As demonstrated, the ethyl acetate extract (EA extract) containing all HAQs and PQS congeners, also induces expression, while AA, the PhnAB product and precursor of all HAQs does not.

lysR-Box is Critical for pqsA-E Transcriptional Activation

Figure 16:
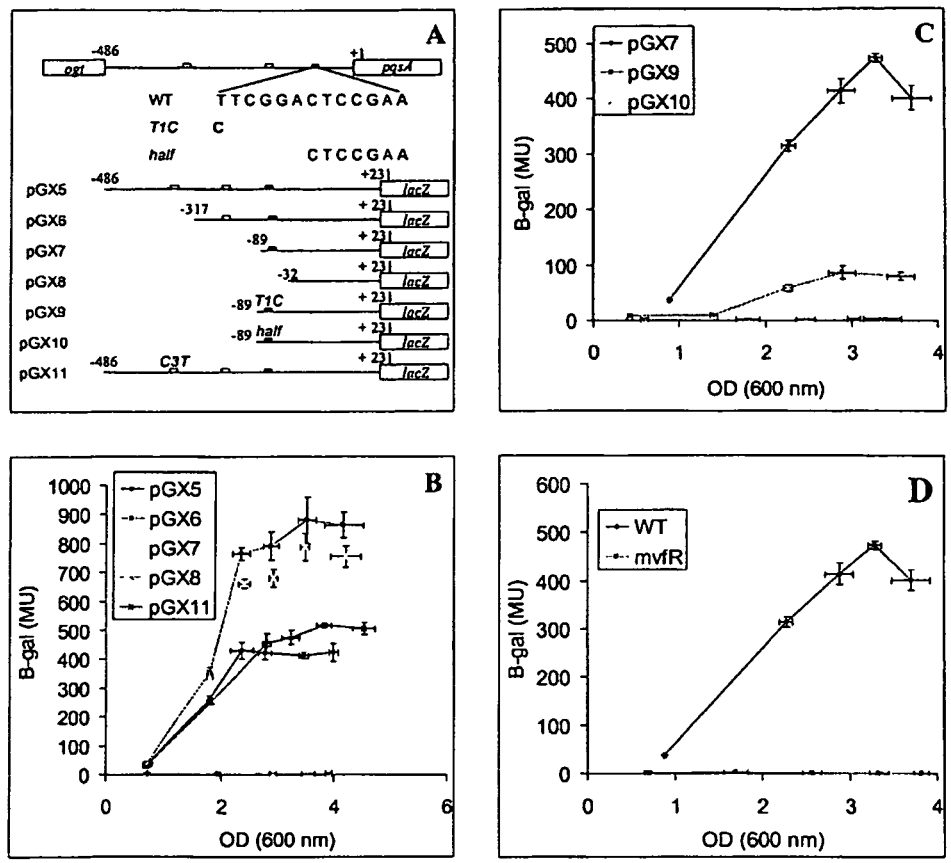
FIG. 16 shows analysis of mutants of the pqsA regulatory region. (A) las-box and lysR box plasmid mutants based on the wild-type pqsA'-lacZ reporter construct, pGX5; (B) PA14 expression of the pqsA-lacZ constucts; (C) PA14 expression of wild type (pGX7) and lysR box mutants; (D) Expression of the pqsA'-lacZ transcriptional reporter pGX7 in PA14, and in an isogenic mvfR mutant.

Our transcriptome studies show MvfR is essential for the transcription of the pqsA-E operon. This operon carries a putative lysR box centered at −45 bp, relative to the pqsA transcription initiation site; and two putative las-box specific palindromic sequence, centered at −311 bp and −151 bp, respectively (FIG. 16A), suggesting that the LasR and/or the RhlR proteins, in addition to MvfR, may bind to the pqsA promoter to regulate pqsA-E transcription. To determine whether the three putative control elements function in pqsA-E regulation, we generated deletion mutants in the pqsA-E regulatory region according to standard methods (FIG. 16). The control plasmid pGX5 contains the segment from −486 relative to the pqsA transcription initiation site through the first 160 (+231) nucleotides of the pqsA gene, and thus presumably the complete pqsA-E regulatory region, fused to lacZ. Beginning with this construct, we then deleted the regions from −486 to −247 bp, −486 to −90 bp, and −486 to −33 bp, to respectively generate pGX6, pGX7, and pGX8. These constructs were then separately introduced into PA14 to assess the importance of the putative las-boxes and lysR-box. FIG. 16B shows that the β-gal activity of pGX5 increases with PA14 cell density; and that deletion of the −486 to −318 bp putative las-box results in increased pqsA transcription, suggesting that a transcription factor(s) binds here to repress pqsA transcription. To determine if the las-box functions in pqsA repression, we used PCR site-directed mutagenesis (Ausubel, F., R. Brent, R. E. Kingston, D. D. Moore, J. G. Seidman, J. A. Smith, and K. Struhl (ed.). 1997. Short protocols in molecular biology, 3rd ed. John Wiley & Sons, Inc., New York, N.Y.) on pGX5 to replace one of the most conserved las-box nucleotides (Whiteley et al., *J. Bacteriol.* 183, 5529-5534, 2001), position 3C, with T (highlighted in grey, FIG. 16A). This substitution does not significantly alter pqsA activation (FIG. 16B). Similarly, deletion of the −317 to −90 bp region does not alter pqsA expression. These results indicate that neither of the putative las-boxes acts in pqsA regulation. In contrast, no pqsA expression occurs when the putative lysR-box is deleted, indicating that the region between −89 and −33 bp is essential for pqsA activation.

To further examine the role of the lysR-box, we modified pGX7 by replacing one of the most conserved nucleotides of the lysR-box, position 1 T, with an A, to generate pGX9; and deleted half of the putative symmetric lysR box, to generate pGX10 (FIG. 16A; T1A and half respectively). These plasmids were then transformed into PA14. FIG. 16C shows that the lysR-box is an essential regulatory element for pqsA activation: the T to A substitution severely reduces, while the half lysR-box deletion completely abrogates, pqsA expression, respectively. This also suggests that the LysR-type transcription factor MvfR activates pqsA-E transcription by binding to the lysR-box, in agreement with our transcriptome data (13), and the observation that pqsA expression is abolished in the mvfR mutant (FIG. 16D).

The above experiments were performed using the following materials and methods.

Materials and Methods

Bacterial Strains, Plasmids and Media.

*P. aeruginosa* strains include: wild type PA14 (Rahme et al., *Science* 268, 1899-1902, 1995); an mvfR mutant (Cao et al., *Proc. Natl. Acad. Sci. USA* 98, 14613-8, 2001); 8C12, a TnphoA-insertion mutant of pqsB (Mahajan-Miklos et al., *Cell* 96, 47-56, 1999); and a lasR::Gm mutant, which was generated by allelic exchange using pSB219.9A as described (Beatson et al., *J Bacteriol* 184, 3598-604, 2002). A pqsE deletion mutant was generated via pEX18Ap allelic replacement, using sucrose selection, resulting in a 570 bp non-polar deletion covering 65% of the sequence (Hoang et al., *Gene* 212, 77-86, 1998). The pqsA (U479) TnphoA mutant was obtained from the PA14 Transposon Insertion Mutant Database. For complementation analysis, mvfR was cloned into pDN18 (Nunn et al., *J. Bacteriol.* 172, 1990). The reporter fusions phzABC-lacZ and hcnA'-lacZ have been described (Whiteley et al., *J. Bacteriol.* 182, 4356-60, 2000; Pessi et al., *J. Bacteriol.* 182, 6940-9, 2000). Plasmids were transformed into PA14 by electroporation (Smith et al., *Nuc. Acid. Res.* 17, 10509, 1989). Specific β-galactosidase activity was determined as reported (Miller, Cold Spring Harbor Laboratory, Cold Spring Harbor, N.Y., pp. 352-355 1972).

Bacteria were grown in Luria-Bertani broth or on 1.5% Bacto-agar (Difco) LB plates. Freshly plated cells served as inoculum. For pyocyanin production, bacteria were grown in King's A broth (King et al., *J. Lab. Clin. Med.* 44, 301, 1954) and the pyocyanin quantified as $OD_{520}$ after supernatant extraction (Essar et al., *J. Bacteriol.* 172, 884-900, 1990). Tetracycline (75 mg/L), carbenicillin (300 mg/L), kanamycin (200 mg/L), and gentamicin (100 mg/L) were included as required.

LC/MS Analysis

Analyses were performed using a Micromass Quattro II triple quadrupole mass spectrometer (Micromass Canada, Pointe-Claire, Can.) in positive electrospray ionization mode, interfaced to an HP1100 HPLC equipped with a 4.5×150 mm reverse phase $C_8$ column. Culture supernatants were twice extracted with ethyl acetate, the solvent was evaporated, and the residue was dissolved in a water/acetonitrile mixture containing the internal standard. Alternatively, culture samples were directly diluted with a methanolic solution of the internal standard, as reported (Lépine et al., *Biochim. Biophys. Acta* 1622, 36-40, 2003).

Synthesis of Labeled HAQ 4-hydroxy-2-heptylquinoline N-oxide (HQNO) was from Sigma. 2,3,4,5-tetradeuteroanthranilic acid ($AA-d_4$) was from CDN isotopes (Pointe-Claire, Canada). The internal standards, 5,6,7,8-tetradeutero-3,4-dihydroxy-2-heptylquinoline ($PQS-d_4$), and 5,6,7,8-tetradeutero-4-hydroxy-2-heptylquinoline ($HHQ-d_4$) were synthesized as reported (Lépine et al., *Biochim. Biophys. Acta* 1622, 36-40, 2003). 5,6,7,8-tetradeutero-4-hydroxy-2-heptylquinoline N-oxide ($HQNO-d_4$) was synthesized from $HHQ-d_4$ (Cornforth et al., *Biochem. J.* 63, 124-130, 1956).

RNA Isolation and Transcriptome Analysis

Whole genome expression profiles were produced in duplicate for PA14 and the mvfR mutant. Cultures were grown in 1 L Erlenmeyer flasks with 100 ml LB at 37° C. and 200 rpm. Cells were sampled at $OD_{600}$=1.5, 2.5, 3.5 and 4.5, and their RNA was immediately stabilized with RNAprotect Bacteria Reagent (Qiagen, Valencia, Calif.) and stored at −80° C. Total RNA was isolated with the RNeasy spin column (including an on-column DNase digestion step) according to the manufacturer (Qiagen), treated with RQ1 DNAse I (Promega, Madison, Wis.) for 1 hr at 37° C., and repurified through an RNeasy column.

Samples were labeled according to the manufacturer (Affymetrix), and hybridized to the Affymetrix GeneChip® *P. aeruginosa* Genome array for 24 hrs at 50° C. using the GeneChip® hybridization oven at 60 rpm. Washing, staining, and scanning were performed according to Affymetrix. The original data files, obtained from the array scans hybridized with the different probes, were converted to cell intensity files (.CEL files) using the Microarray Suite 5.0. Data analysis/clustering was performed with the DNA-Chip Analyzer (dCHIP) software (Li et al., *Proc. Natl. Acad. Sci. USA* 98, 31-36, 2001).

Antimicrobial Activity Assay

HAQ antimicrobial activity was evaluated on well-plates. An overnight culture (30 µl) was plated to produce a bacterial lawn, and 5 mm diameter holes were punched in the agar and filled with 60 µl of a 25% methanol solution of test extract or pure HAQ. Plates were incubated overnight at 37° C. and scored for growth inhibition zones around the test wells.

Cell-To-Cell Communication Assay

To test if *P. aeruginosa* cells produce PQS in response to HHQ released by other cells, we compared the concentrations of PQS in cultures, grown in 30 ml LB in 250 ml flasks, of a lasR mutant, to co-cultures containing 50% of a lasR mutant and an mvfR mutant. pDN18mvfR was introduced into the lasR mutant to compensate for the lower expression of mvfR in this background. The effect on gene expression of exogenous HHQ was assayed by comparing the β-galactosidase activity of PA14 versus lasR− cells carrying the phzABC-lacZ or hcnA'-lacZ fusions, grown in the absence or presence of 10 mg/L of HHQ.

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying a compound that reduces production of a 4-hydroxy-2-alkylquinoline (HAQ) molecule, 4-hydroxy-2-heptylquinoline (HHQ) molecule, or a derivative or precursor thereof, said method comprising:
(a) contacting a *Pseudomonas* cell with a compound;
(b) measuring the production of a molecule selected from the group consisting of a HAQ molecule, HHQ molecule, or a derivative or precursor thereof in said *Pseudomonas* cell; and
(c) comparing the production of said molecule in step (b) relative to production of said molecule by said *Pseudomonas* cell when not contacted with said compound, thereby identifying said compound tha reduces production of said HAQ molecule, HHQ molecule, or a derivative or precursor thereof, wherein said HAQ molecule, said HHQ molecule, or said derivative or precursor thereof is selected from any one of the following:

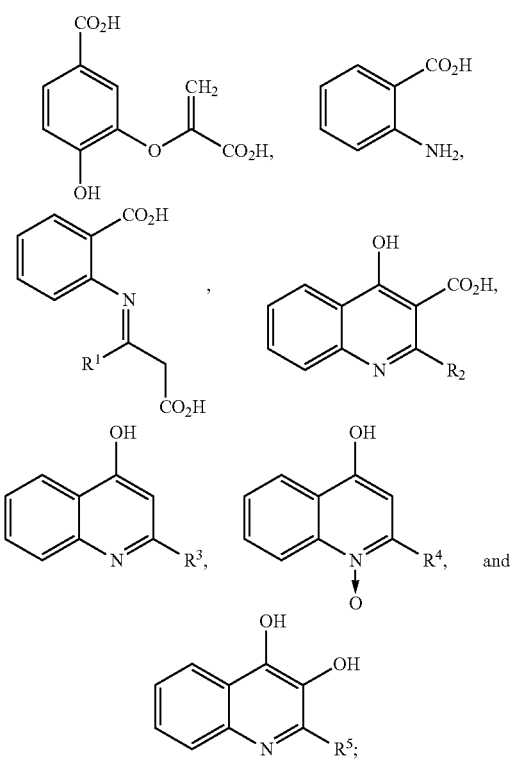

wherein $R^1$, $R^2$, and $R^4$ are independently —$C_5H_{11}$, —$C_6H_{13}$, —$C_7H_{15}$, —$C_8H_{17}$, —$C_9H_{19}$, —$C_{11}H_{23}$, —$C_7H_{13}$, —$C_8H_{15}$, —$C_9H_{17}$, or —$C_{11}H_{21}$;

$R^3$ is —$C_5H_{11}$, —$C_6H_{13}$, —$C_7H_{15}$, —$C_8H_{17}$, —$C_9H_{19}$, —$C_{11}H_{23}$, —$C_9H_{17}$, or —$C_{11}H_{21}$;

$R^5$ is —$C_5H_{11}$, —$C_6H_{13}$, —$C_7H_{15}$, —$C_8H_{17}$, —$C_9H_{19}$, or —$C_{11}H_{23}$.

2. The method of claim 1, wherein step (b) comprises measuring the HAQ molecule.

3. The method of claim 1, wherein said *Pseudomonas* cell infects a mammal.

4. The method of claim 3, wherein said mammal is a human.

5. The method of claim 1, wherein said *Pseudomonas* cell infects a plant.

6. The method of claim 1, wherein said *Pseudomonas* cell is *Pseudomonas aeruginosa*.

7. The method of claim 6, wherein said *Pseudomonas aeruginosa* is *Pseudomonas aeruginosa* PA14 or *Pseudomonas aeruginosa* PA01.

8. The method of claim 1, wherein said molecule is selected from the group consisting of

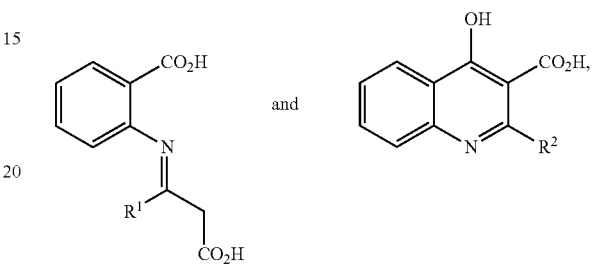

wherein $R^1$ and $R^2$ are independently —$C_5H_{11}$, —$C_6H_{13}$, —$C_7H_{15}$, —$C_8H_{17}$, —$C_9H_{19}$, —$C_{11}H_{23}$, —$C_7H_{13}$, —$C_8H_{15}$, —$C_9H_{17}$, or —$C_{11}H_{21}$.

9. The method of claim 1, wherein said HHQ is

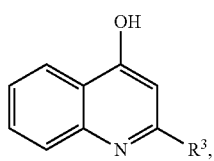

wherein $R^3$ is —$C_5H_{11}$, —$C_6H_{13}$, —$C_7H_{15}$, —$C_8H_{17}$, —$C_9H_{19}$, —$C_{11}H_{23}$, —$C_9H_{17}$, or —$C_{11}H_{21}$.

* * * * *

UNITED STATES PATENT AND TRADEMARK OFFICE
CERTIFICATE OF CORRECTION

PATENT NO.       : 8,906,602 B2                                 Page 1 of 1
APPLICATION NO.  : 10/586403
DATED            : December 9, 2014
INVENTOR(S)      : Laurence G. Rahme et al.

It is certified that error appears in the above-identified patent and that said Letters Patent is hereby corrected as shown below:

Claims

Column 48, Claim 1, Line 61, replace "tha" with --that--.

Column 49, Claim 1, Line 37, replace "$-C_8{}^{17}$," with -- $–C_8H_{17}$,--.

Signed and Sealed this
Twenty-seventh Day of October, 2015

Michelle K. Lee
*Director of the United States Patent and Trademark Office*

```
                             SEQUENCE LISTING

<160> NUMBER OF SEQ ID NOS: 17

<210> SEQ ID NO 1
<211> LENGTH: 1554
<212> TYPE: DNA
<213> ORGANISM: Pseudomonas aeruginosa

<400> SEQUENCE: 1
atgtccacat tggccaacct gaccgaggtt ctgttccgcc tcgatttcga tcccgatacc      60
gccgtttatc actatcgggg ccagactctc agccggctgc aatgccggac ctacattctc     120
tcccaggcca gccaactggc ccgcctgctc aagcccggcg atcgcgtggt gctggcgttg     180
aacgactcgc cttcgctggc ctgcctgttc ctggcctgca tcgcggtcgg cgccattccc     240
gccgtgatca atcccaagtc ccgcgagcag gccctggccg atatcgctgc cgactgccag     300
gccagcctgg tggtgcgtga agccgatgca ccgtcgctga gcggtccttt ggcgccgttg     360
accctgcgtg cggccgccgg acgccctttg ctcgacgatt tctcgctgga cgcgctggtc     420
ggccctgcgg acctcgattg gagtgccttc catcgccagg acccggcggc agcctgtttc     480
ctgcaataca cctcgggttc caccggggcg cccaaggggg tgatgcacag cctgcgcaac     540
acgctcggtt tctgccgggc gttcgctacg gagttgctgg cattgcaggc gggagaccgg     600
ctgtattcga ttcccaagat gttcttcggc tatggcatgg caacagcct gttctttccc      660 tggttcagcg gagcctcggc gctgctcgac gatacctggc cgagcccgga gcgggttctg     720
gagaacctgt tcgccttccg cccccgggtc ctgtttgggg tgccggccat ctatgcctcg     780
ctgcgtccgc aggccaggga gctgttgagc agcgtgcgcc tggcgttttc cgccggctcg     840
ccgctgccgc gcggcgagtt cgaattctgg gccgcgcacg ggctggagat ctgcgacggc     900
atcggggcta ccgaggtcgg ccatgtgttc ctcgccaacc gcccgggcca ggcgcgtgcc     960
gacagcaccg ggctgccgtt gcctggctat gagtgccggc tggtggaccg cgaaggacac    1020
actatcgagg aagcgggccg gcaaggcgtg ctgttggtgc gtggcccagg gctgagtccg    1080
ggttactggc gggccagcga agagcagcag gcgcgcttcg caggtggctg gtaccgcacc    1140
ggcgacctgt tcgagcgcga cgagtcgggt gcctaccgtc actgtgggcg ggaagacgat    1200
ctgttcaagg tgaatggccg ctgggtggtg ccgacccagg tcgagcaggc gatctgccgt    1260
catctgccgg aagtgagcga ggcggttctg gttcctacct gccggctgca cgacggcttg    1320
cgtccgaccc tgttcgtcac cctggccact ccgctggacg acaaccagat cctgctggcg    1380
cagcgcatcg accagcatct cgccgaacag attccctcgc acatgctgcc cagccaattg    1440
catgtgctgc cggccttgcc gcgcaacgac aacggcaagt tggcgcgcgc cgagctgcgc    1500
cacctggccg acaccctta tcacgacaac cttccggagg aacgggcatg ttga           1554

<210> SEQ ID NO 2
<211> LENGTH: 852
<212> TYPE: DNA
<213> ORGANISM: Pseudomonas aeruginosa

<400> SEQUENCE: 2
atgttgattc aggctgtggg ggtgaacctg cccccatcct atgtgtgtct ggaggggccg      60
ctgggaggcg aacgccctcg cgcccagggc gacgagatgc tgatgcagcg cttgctgccg     120
```

```
gcggttcgcg aagccctgga cgaggcggcg gtcaagcccg aggagatcga cctgatcgtc      180
ggcctcgccc tgtctcccga ccatctgatc gagaaccgcg acatcatggc gccgaagatc      240
ggccatccgt tgcagaaggt cctcggcgcg aatcgcgcgc atgtcttcga cctcaccgac      300
tcgagcctgg cccgcgccct ctacgtggtc gataccctcg ccagcgacca gggctatcgc      360
aacgtcctgg tcgtgcgcgg cgaatccagc cagggattgg aagtggacag cgagtccggc      420
ttcgcccttg ccgacggcgc cctggcgctg ctctgccggc cgaccggcaa ggccgcgttc      480
cgtcgcggtg cgctgggcgg tgatccggcg caggaatggc tgccgctgag cattccgctg      540
aataccgata ttcgccaggt aggcgacgtc aaggacacc tcaacctgcc ggcccaacct       600
ggattgcccg aagcggtacg cgccggattc accgtctgg ccggggactt cccgcaactg       660
aactgggtgc gcgaggaatg gttcggccag ggacggcccg atggtcgttg cctggggccg      720
ttcgaactgg cgtcgcaact gcgcgcggca cagcgcgacc gtctggatga actgctgctg      780
atcagcttcg atccgttcgg catggtggtg gagggcgtga ccctggaact ggcgggagaa      840
gctcatgcat aa                                                           852

<210> SEQ ID NO 3
<211> LENGTH: 1047
<212> TYPE: DNA
<213> ORGANISM: Pseudomonas aeruginosa

<400> SEQUENCE: 3
atgcataagg tcaaactggc agcgatcacc tgtgaacttc cggctcgcag ctacgaaaac       60
gacgatccgg tgttcgctgc ggtaccggac ctcagcgagt cctggtggca attctggggc      120
gtcaatcggc ggggctattt cgacccgcgg aacggcgaga cgagttcag cctggtggtc       180 cgggccgccg agcgcctgct gcgtagcagc gataccgcgc ggatagcgt ggacatgctg       240 atctgttcgg cttcctcgcc gatcatgacc gacgccggcg atgtcctgcc ggacctgcgc      300
ggacgtctct acccgcgcat ggccaacgtg ctgtccaagc agctcggcct gagtcgggcg      360
ctgccattgg attcgcagat ggagtgcgcc agcttcctgc tcaacctgcg cctggcagcg      420
agcatgatcc gccagggtaa ggccgagaaa gtgctggtgg tgtgcagcga gtacatctcc      480
aacctgctcg acttcacctc gcgtacctcg accctgttcg ccgatggctg cgcggtggcc      540
ctgctgaccc gcgcgacga tgacagctgc gacctgctgc cttcggccga acacagcgac      600
gctacgttct atgaagtggc caccggtcgc tggcgcctgc cggaaaaccc gaccggcgag      660
gccaagccgc ggctttattt ctcgttgttc agcgacggcc agaacaagat ggccagcttc      720
gttccgacca acgtgccgat cgcgatgcgc cgggcgttgg aaaaggccgg cctgggcagc      780
gatgacatcg attatttcgt cttccaccag ccagcgccgt tcctggtcaa ggcctgggcc      840
gagggcatcg gtgcccgtcc tgagcagtac caactgacga tgggcgatac cggcgtgatg      900
atctccgttt ccatcccgta caccctgatg accggcctgc gcgagggcaa gatccgcccc      960
ggcgatcgta tcgtcatggc cggcgcagcc actggctggg ggttcgccgc ccaggtctgg     1020
caattgggtg aggtgctggt gtgctga                                        1047

<210> SEQ ID NO 4
<211> LENGTH: 1014
<212> TYPE: DNA
<213> ORGANISM: Pseudomonas aeruginosa

<400> SEQUENCE: 4
```

```
atgggtaatc cgatcctggc cgggctgggt ttcagcctgc cgaaacgcca ggtcagcaat    60
catgacctgg tagggcgcat caatacgtcg gacgagttca tcgtcgaacg taccggcgtg   120
cgcacccgct atcacgtcga gccggaacag gcggtcagcg cgctgatggt gccggcggcg   180
cgccaggcca tcgaggctgc cgggctgctg ccggaggaca tcgacctgtt gctggtgaac   240
accctgtcgc cggaccacca cgacccgtcc caggcctgcc tgatccagcc gctgctgggc   300
ctgcggcaca tcccggtact ggatatccgg gcacagtgca gcgggttgct gtacggcttg   360
cagatggctc gcgggcagat cctcgccggg ctggcacggc atgtcctggt ggtctgcggc   420
gaggtgctgt ccaagcgcat ggactgttcg gaccgcggcc gcaacctgtc gatcctgctc   480
ggcgacggtg ccggcgcagt ggtggtcagc gccggcgaga gtctcgaaga cggactgctg   540
gacctgcgcc tgggcgccga cggcaactac ttcgacctgc tgatgaccgc ggcgccgggt   600
agtgcctcgc cgaccttcct cgacgagaat gtcctgcgcg agggcggggg cgagttcctc   660
atgcgcggcc ggccgatgtt cgagcatgcc agccagaccc tggtacggat cgccggcgaa   720
atgctcgcgg cccatgagct gaccctggac gacatcgacc atgtgatctg ccatcaaccg   780
aacctgcgca tcctcgatgc ggtgcaggag caactgggca ttccccagca caagttcgcg   840
gtgaccgtga tcgtctgggg caacatggct tcggcctcga ccccggtcac gctggcgatg   900
ttctggccgg acatccagcc gggacagcgg gtgctggtcc tgacctacgg ctccggcgcg   960
acctggggcg cggcgctgta ccgcaaacct gaggaggtga accggccatg ttga         1014

<210> SEQ ID NO 5
<211> LENGTH: 906
<212> TYPE: DNA
<213> ORGANISM: Pseudomonas aeruginosa

<400> SEQUENCE: 5
atgttgaggc tttcggctcc cggtcaactg gatgatgacc tgtgcctgtt ggggacgtc    60
caggtgccgg tgttcctgct gcgtctcggt gaggcgagct gggcgctggt tgaaggaggg   120
atcagccggg atgccgaatt ggtttgggcg gacctgtgcc gctgggtcgc gacccgtcc   180
caggtgcact actggctgat cacccacaag cactacgacc actgcggcct gctgccctac   240
ctgtgtccgc ggctgccgaa cgtacaggtc ctggcgtccg agcggacctg ccaggcctgg   300
aagtcggaaa gcgcggtgcg ggtggtcgag cgcttgaacc ggcaactgtt gcgtgcggag   360
cagcggttgc ccgaggcctg tgcctgggac gctctgccgg ttcgcgcggt ggccgacggc   420
gagtggctgg agctgggacc gcggcatcgc ctgcaggtca tagaggccca cggccacagc   480
gacgatcacg tggttttcta cgacgtgcga cgccgacgcc tgttctgcgg cgatgccctg   540
ggcgagttcg acgaggcaga gggggtgtgg cggccgctgg tgttcgacga catggaggct   600
tacctggagt ccctggaacg tctgcagcgt ctgccgaccc tgctgcaact gatcccggga   660
cacggcggcc tgctgcgggg gcggctggcc gcggatgggg ccgagtcggc ctataccgag   720
tgtctgcgcc tgtgccggcg gttgctctgg cgccagtcca tgggcgaatc cctcgacgaa   780
ctgagcgagg agctgcaccg cgcctggggt gggcagagcg tcgacttcct gcccggcgaa   840
ctgcacctgg ggagcatgcg ccggatgctg gagattctct cccgccaggc gctgcctctg   900
gactga                                                              906

<210> SEQ ID NO 6
<211> LENGTH: 1149
<212> TYPE: DNA
<213> ORGANISM: Pseudomonas aeruginosa
```

<400> SEQUENCE: 6

```
atgaccgttc ttatccaggg ggccgggatc gccggcctgg cgctggcgcg cgaattcacc        60
aaggcaggca tcgactggct gctggtcgag cgggccagcg agatcaggcc catcggtacc       120
ggcatcaccc tggcgagcaa tgcgttgacg gcgttgtcca gcaccctgga tctcgaccgg       180
ctgttccgcc gtggcatgcc gttggccggc atcaacgtat acgcccacga cggttcgatg       240
ctgatgtcga tgccttccag tctgggtggg aattcccgcg cggcctggc gttgcagcgc        300
cacgaactgc atgcggcgct actggagggg ctggatgagt cgcgcattcg ggtcggggtc       360
tccatcgtcg agatcctcga cggactcgac cacgaacgcg tgaccctgag cgacggcact       420
gtccacgact gttcgctggt ggtcggtgcg gatggcattc gttcgagcgt gcgacgttat       480
gtctggccgg aggcgacctt gcgtcattcc ggcgaaacct gctggcgcct ggtcgttccc       540
catcggctgg aggacgccga gctggcggga gaggtctggg gcacggcaa gcgcctcggc        600
ttcatccaga tcagcccgcg cgagatgtat gtctacgcga ccctgaaggt gcgccgggag       660
gagcccgagg acgaggaggg cttcgtaacc ccgcaacggc tggccgccca ctacgcggac       720
ttcgacggca tcgcgcgag catcgcccgg ctcataccga cgccaccac gctggtgcac         780
aacgacctcg aggagttggc cggcgcctcc tggtgccgcg gacgggtagt gctgatcggt       840
gacgccgcac acgccatgac gccgaacctg ggcagggcg cggccatggc cctggaggac        900
gccttcctgc tggcgcgcct gtggtgcctg cgccgcgcg ccgagacgct gatcctgttc        960
cagcagcaac gcgaggcgcg gatcgagttc atcaggaagc aatcctggat cgtcggccgc      1020
cttggtcagt gggaatcgcc ctggagcgtc tggctgagga ataccctcgt tcgcctggtg      1080
ccgaatgcca gtcgcaggcg cctccaccag cgtcttttca ccggtgtcgg tgagatggcc      1140
gcacagtag                                                              1149
```

<210> SEQ ID NO 7
<211> LENGTH: 1197
<212> TYPE: DNA
<213> ORGANISM: Pseudomonas aeruginosa

<400> SEQUENCE: 7

```
atgacggaca accatatcga tgtactgatc aacggctgcg gcatcggcgg ggcgatgctc        60
gcctacctgc tcggccgcca gggccaccgc gtggtgtag tggaacaggc acggcgcgaa        120
cgcgcgatca acggcgccga cctgctcaag ccggccggca tccgggtggt cgaggcggcc       180
gggttgttgg ccgaggtgac ccgtcgcggt gggcgggtcc gccatgagct ggaggtctat       240
cacgacggcg agctgcttcg ctatttcaac tattccagcg tcgacgcgcg cggctatttc       300
atcctcatgc cctgcgagtc gctgcgccgc tggtactgg aaaaaatcga cggcgaagcg        360
accgtcgaga tgctgttcga cccgcatc gaagcggtgc agcgcgacga cgccacgcg          420
atcgaccagg tgcgcctgaa cgacggccgc gtgctgcgtc gcgggtggt ggtgggagcc        480
gacggtatcg cctcctacgt gcgccgccgg ctgctcgata tcgatgtgga acgccgcccc       540
tacccgtcgc cgatgctggt cggcaccttc gccctggcgc cctgcgtggc cgagcgcaac       600
cgcctgtacg tggactcgca gggcgggctg gcctacttct atccgatcgg tttcgaccgc       660
gcgcgactgg tggtgagctt ccccagggag gaggcgcgcg agctgatggc cgacacccgc       720
ggcgagtcgc tgccggcg cttgcaacgc ttcgtcggcg acgagagcgc cgaggcgatc         780
gccgccgtca ccggcacttc gcgcttcaag ggcatccca tcggctacct gaacctggac        840
```

-continued

```
cgctactggg cggacaacgt ggcgatgctc ggcgacgcca tccacaacgt gcatccgatc    900
accggccagg gcatgaacct ggccatcgag gacgccagcg ccctggccga cgccctcgac    960
ctggccttgc gcgacgcctg cgcgctggag gatgccctgg ccggctacca ggccgagcgc   1020
ttcccggtga accaggcgat cgtctcctat ggccatgcgt tggccaccag cctggaggat   1080
cgccagcgct tcgccggggt cttcgacacc gccctgcagg gcagcagccg tacgccggaa   1140
gccctgggcg gcgagcgctc ctaccagccg gtgcggtcgc cggcgccgct cggctga      1197
```

<210> SEQ ID NO 8
<211> LENGTH: 517
<212> TYPE: PRT
<213> ORGANISM: Pseudomonas aeruginosa

<400> SEQUENCE: 8

```
Met Ser Thr Leu Ala Asn Leu Thr Glu Val Leu Phe Arg Leu Asp Phe
 1               5                  10                  15

Asp Pro Asp Thr Ala Val Tyr His Tyr Arg Gly Gln Thr Leu Ser Arg
                20                  25                  30

Leu Gln Cys Arg Thr Tyr Ile Leu Ser Gln Ala Ser Gln Leu Ala Arg
            35                  40                  45

Leu Leu Lys Pro Gly Asp Arg Val Val Leu Ala Leu Asn Asp Ser Pro
        50                  55                  60

Ser Leu Ala Cys Leu Phe Leu Ala Cys Ile Ala Val Gly Ala Ile Pro
65                  70                  75                  80

Ala Val Ile Asn Pro Lys Ser Arg Glu Gln Ala Leu Ala Asp Ile Ala
                85                  90                  95

Ala Asp Cys Gln Ala Ser Leu Val Val Arg Glu Ala Asp Ala Pro Ser
            100                 105                 110

Leu Ser Gly Pro Leu Ala Pro Leu Thr Leu Arg Ala Ala Ala Gly Arg
        115                 120                 125

Pro Leu Leu Asp Asp Phe Ser Leu Asp Ala Leu Val Gly Pro Ala Asp
    130                 135                 140

Leu Asp Trp Ser Ala Phe His Arg Gln Asp Pro Ala Ala Ala Cys Phe
145                 150                 155                 160

Leu Gln Tyr Thr Ser Gly Ser Thr Gly Ala Pro Lys Gly Val Met His
                165                 170                 175

Ser Leu Arg Asn Thr Leu Gly Phe Cys Arg Ala Phe Ala Thr Glu Leu
            180                 185                 190

Leu Ala Leu Gln Ala Gly Asp Arg Leu Tyr Ser Ile Pro Lys Met Phe
        195                 200                 205

Phe Gly Tyr Gly Met Gly Asn Ser Leu Phe Phe Pro Trp Phe Ser Gly
    210                 215                 220

Ala Ser Ala Leu Leu Asp Asp Thr Trp Pro Ser Pro Glu Arg Val Leu
225                 230                 235                 240

Glu Asn Leu Val Ala Phe Arg Pro Arg Val Leu Phe Gly Val Pro Ala
                245                 250                 255

Ile Tyr Ala Ser Leu Arg Pro Gln Ala Arg Glu Leu Leu Ser Ser Val
            260                 265                 270

Arg Leu Ala Phe Ser Ala Gly Ser Pro Leu Pro Arg Gly Glu Phe Glu
        275                 280                 285

Phe Trp Ala Ala His Gly Leu Glu Ile Cys Asp Gly Ile Gly Ala Thr
    290                 295                 300

Glu Val Gly His Val Phe Leu Ala Asn Arg Pro Gly Gln Ala Arg Ala
305                 310                 315                 320
```

```
Asp Ser Thr Gly Leu Pro Leu Pro Gly Tyr Glu Cys Arg Leu Val Asp
            325                 330                 335

Arg Glu Gly His Thr Ile Glu Ala Gly Arg Gln Gly Val Leu Leu
            340                 345                 350

Val Arg Gly Pro Gly Leu Ser Pro Gly Tyr Trp Arg Ala Ser Glu Glu
            355                 360                 365

Gln Gln Ala Arg Phe Ala Gly Gly Trp Tyr Arg Thr Gly Asp Leu Phe
            370                 375                 380

Glu Arg Asp Glu Ser Gly Ala Tyr Arg His Cys Gly Arg Glu Asp Asp
385                 390                 395                 400

Leu Phe Lys Val Asn Gly Arg Trp Val Val Pro Thr Gln Val Glu Gln
                405                 410                 415

Ala Ile Cys Arg His Leu Pro Glu Val Ser Glu Ala Val Leu Val Pro
            420                 425                 430

Thr Cys Arg Leu His Asp Gly Leu Arg Pro Thr Leu Phe Val Thr Leu
            435                 440                 445

Ala Thr Pro Leu Asp Asp Asn Gln Ile Leu Leu Ala Gln Arg Ile Asp
            450                 455                 460

Gln His Leu Ala Glu Gln Ile Pro Ser His Met Leu Pro Ser Gln Leu
465                 470                 475                 480

His Val Leu Pro Ala Leu Pro Arg Asn Asp Asn Gly Lys Leu Ala Arg
                485                 490                 495

Ala Glu Leu Arg His Leu Ala Asp Thr Leu Tyr His Asp Asn Leu Pro
            500                 505                 510

Glu Glu Arg Ala Cys
            515

<210> SEQ ID NO 9
<211> LENGTH: 283
<212> TYPE: PRT
<213> ORGANISM: Pseudomonas aeruginosa

<400> SEQUENCE: 9

Met Leu Ile Gln Ala Val Gly Val Asn Leu Pro Pro Ser Tyr Val Cys
1               5                   10                  15

Leu Glu Gly Pro Leu Gly Gly Glu Arg Pro Arg Ala Gln Gly Asp Glu
                20                  25                  30

Met Leu Met Gln Arg Leu Leu Pro Ala Val Arg Glu Ala Leu Asp Glu
            35                  40                  45

Ala Ala Val Lys Pro Glu Glu Ile Asp Leu Ile Val Gly Leu Ala Leu
        50                  55                  60

Ser Pro Asp His Leu Ile Glu Asn Arg Asp Ile Met Ala Pro Lys Ile
65                  70                  75                  80

Gly His Pro Leu Gln Lys Val Leu Gly Ala Asn Arg Ala His Val Phe
                85                  90                  95

Asp Leu Thr Asp Ser Ser Leu Ala Arg Ala Leu Tyr Val Val Asp Thr
            100                 105                 110

Leu Ala Ser Asp Gln Gly Tyr Arg Asn Val Leu Val Arg Gly Glu
            115                 120                 125

Ser Ser Gln Gly Leu Glu Val Asp Ser Glu Ser Gly Phe Ala Leu Ala
            130                 135                 140

Asp Gly Ala Leu Ala Leu Leu Cys Arg Pro Thr Gly Lys Ala Ala Phe
145                 150                 155                 160

Arg Arg Gly Ala Leu Gly Gly Asp Pro Ala Gln Glu Trp Leu Pro Leu
```

```
                165                 170                 175
Ser Ile Pro Leu Asn Thr Asp Ile Arg Gln Val Gly Asp Val Lys Gly
            180                 185                 190

His Leu Asn Leu Pro Ala Gln Pro Gly Leu Pro Glu Ala Val Arg Ala
            195                 200                 205

Gly Phe Thr Arg Leu Ala Gly Asp Phe Pro Gln Leu Asn Trp Val Arg
    210                 215                 220

Glu Glu Trp Phe Gly Gln Gly Arg Pro Asp Gly Arg Cys Leu Gly Pro
225                 230                 235                 240

Phe Glu Leu Ala Ser Gln Leu Arg Ala Ala Gln Arg Asp Arg Leu Asp
                245                 250                 255

Glu Leu Leu Leu Ile Ser Phe Asp Pro Phe Gly Met Val Val Glu Gly
            260                 265                 270

Val Thr Leu Glu Leu Ala Gly Glu Ala His Ala
            275                 280

<210> SEQ ID NO 10
<211> LENGTH: 348
<212> TYPE: PRT
<213> ORGANISM: Pseudomonas aeruginosa

<400> SEQUENCE: 10

Met His Lys Val Lys Leu Ala Ala Ile Thr Cys Glu Leu Pro Ala Arg
1               5                   10                  15

Ser Tyr Glu Asn Asp Asp Pro Val Phe Ala Ala Val Pro Asp Leu Ser
            20                  25                  30

Glu Ser Trp Trp Gln Phe Trp Gly Val Asn Arg Arg Gly Tyr Phe Asp
        35                  40                  45

Pro Arg Asn Gly Glu Asn Glu Phe Ser Leu Val Val Arg Ala Ala Glu
    50                  55                  60

Arg Leu Leu Arg Ser Ser Asp Thr Ala Pro Asp Ser Val Asp Met Leu
65                  70                  75                  80

Ile Cys Ser Ala Ser Ser Pro Ile Met Thr Asp Ala Gly Asp Val Leu
                85                  90                  95

Pro Asp Leu Arg Gly Arg Leu Tyr Pro Arg Met Ala Asn Val Leu Ser
            100                 105                 110

Lys Gln Leu Gly Leu Ser Arg Ala Leu Pro Leu Asp Ser Gln Met Glu
        115                 120                 125

Cys Ala Ser Phe Leu Leu Asn Leu Arg Leu Ala Ala Ser Met Ile Arg
130                 135                 140

Gln Gly Lys Ala Glu Lys Val Leu Val Val Cys Ser Glu Tyr Ile Ser
145                 150                 155                 160

Asn Leu Leu Asp Phe Thr Ser Arg Thr Ser Thr Leu Phe Ala Asp Gly
                165                 170                 175

Cys Ala Val Ala Leu Leu Thr Arg Gly Asp Asp Asp Ser Cys Asp Leu
            180                 185                 190

Leu Ala Ser Ala Glu His Ser Asp Ala Thr Phe Tyr Glu Val Ala Thr
        195                 200                 205

Gly Arg Trp Arg Leu Pro Glu Asn Pro Thr Gly Glu Ala Lys Pro Arg
    210                 215                 220

Leu Tyr Phe Ser Leu Phe Ser Asp Gly Gln Asn Lys Met Ala Ser Phe
225                 230                 235                 240

Val Pro Thr Asn Val Pro Ile Ala Met Arg Arg Ala Leu Glu Lys Ala
                245                 250                 255
```

Gly Leu Gly Ser Asp Asp Ile Asp Tyr Phe Val Phe His Gln Pro Ala
            260                 265                 270

Pro Phe Leu Val Lys Ala Trp Ala Glu Gly Ile Gly Ala Arg Pro Glu
        275                 280                 285

Gln Tyr Gln Leu Thr Met Gly Asp Thr Gly Val Met Ile Ser Val Ser
    290                 295                 300

Ile Pro Tyr Thr Leu Met Thr Gly Leu Arg Glu Gly Lys Ile Arg Pro
305                 310                 315                 320

Gly Asp Arg Ile Val Met Ala Gly Ala Thr Gly Trp Gly Phe Ala
                325                 330                 335

Ala Gln Val Trp Gln Leu Gly Val Leu Val Cys
            340                 345

<210> SEQ ID NO 11
<211> LENGTH: 337
<212> TYPE: PRT
<213> ORGANISM: Pseudomonas aeruginosa

<400> SEQUENCE: 11

Met Gly Asn Pro Ile Leu Ala Gly Leu Gly Phe Ser Leu Pro Lys Arg
1               5                   10                  15

Gln Val Ser Asn His Asp Leu Val Gly Arg Ile Asn Thr Ser Asp Glu
            20                  25                  30

Phe Ile Val Glu Arg Thr Gly Val Arg Thr Arg Tyr His Val Glu Pro
        35                  40                  45

Glu Gln Ala Val Ser Ala Leu Met Val Pro Ala Ala Arg Gln Ala Ile
    50                  55                  60

Glu Ala Ala Gly Leu Leu Pro Glu Asp Ile Asp Leu Leu Leu Val Asn
65                  70                  75                  80

Thr Leu Ser Pro Asp His His Asp Pro Ser Gln Ala Cys Leu Ile Gln
                85                  90                  95

Pro Leu Leu Gly Leu Arg His Ile Pro Val Leu Asp Ile Arg Ala Gln
            100                 105                 110

Cys Ser Gly Leu Leu Tyr Gly Leu Gln Met Ala Arg Gly Gln Ile Leu
        115                 120                 125

Ala Gly Leu Ala Arg His Val Leu Val Val Cys Gly Glu Val Leu Ser
    130                 135                 140

Lys Arg Met Asp Cys Ser Asp Arg Gly Arg Asn Leu Ser Ile Leu Leu
145                 150                 155                 160

Gly Asp Gly Ala Gly Ala Val Val Val Ser Ala Gly Glu Ser Leu Glu
                165                 170                 175

Asp Gly Leu Leu Asp Leu Arg Leu Gly Ala Asp Gly Asn Tyr Phe Asp
            180                 185                 190

Leu Leu Met Thr Ala Ala Pro Gly Ser Ala Ser Pro Thr Phe Leu Asp
        195                 200                 205

Glu Asn Val Leu Arg Glu Gly Gly Gly Glu Phe Leu Met Arg Gly Arg
    210                 215                 220

Pro Met Phe Glu His Ala Ser Gln Thr Leu Val Arg Ile Ala Gly Glu
225                 230                 235                 240

Met Leu Ala Ala His Glu Leu Thr Leu Asp Asp Ile Asp His Val Ile
                245                 250                 255

Cys His Gln Pro Asn Leu Arg Ile Leu Asp Ala Val Gln Glu Gln Leu
            260                 265                 270

Gly Ile Pro Gln His Lys Phe Ala Val Thr Val Asp Arg Leu Gly Asn
        275                 280                 285

```
Met Ala Ser Ala Ser Thr Pro Val Thr Leu Ala Met Phe Trp Pro Asp
        290                 295                 300

Ile Gln Pro Gly Gln Arg Val Leu Val Leu Thr Tyr Gly Ser Gly Ala
305                 310                 315                 320

Thr Trp Gly Ala Ala Leu Tyr Arg Lys Pro Glu Glu Val Asn Arg Pro
                325                 330                 335

Cys

<210> SEQ ID NO 12
<211> LENGTH: 301
<212> TYPE: PRT
<213> ORGANISM: Pseudomonas aeruginosa

<400> SEQUENCE: 12

Met Leu Arg Leu Ser Ala Pro Gly Gln Leu Asp Asp Leu Cys Leu
 1               5                  10                  15

Leu Gly Asp Val Gln Val Pro Val Phe Leu Arg Leu Gly Glu Ala
                20                  25                  30

Ser Trp Ala Leu Val Glu Gly Gly Ile Ser Arg Asp Ala Glu Leu Val
                35                  40                  45

Trp Ala Asp Leu Cys Arg Trp Val Ala Asp Pro Ser Gln Val His Tyr
50                  55                  60

Trp Leu Ile Thr His Lys His Tyr Asp His Cys Gly Leu Leu Pro Tyr
65                  70                  75                  80

Leu Cys Pro Arg Leu Pro Asn Val Gln Val Leu Ala Ser Glu Arg Thr
                85                  90                  95

Cys Gln Ala Trp Lys Ser Glu Ser Ala Val Arg Val Glu Arg Leu
                100                 105                 110

Asn Arg Gln Leu Leu Arg Ala Glu Gln Arg Leu Pro Glu Ala Cys Ala
                115                 120                 125

Trp Asp Ala Leu Pro Val Arg Ala Val Ala Asp Gly Glu Trp Leu Glu
        130                 135                 140

Leu Gly Pro Arg His Arg Leu Gln Val Ile Glu Ala His Gly His Ser
145                 150                 155                 160

Asp Asp His Val Val Phe Tyr Asp Val Arg Arg Arg Leu Phe Cys
                165                 170                 175

Gly Asp Ala Leu Gly Glu Phe Asp Glu Ala Gly Val Trp Arg Pro
                180                 185                 190

Leu Val Phe Asp Asp Met Glu Ala Tyr Leu Glu Ser Leu Glu Arg Leu
                195                 200                 205

Gln Arg Leu Pro Thr Leu Leu Gln Leu Ile Pro Gly His Gly Gly Leu
        210                 215                 220

Leu Arg Gly Arg Leu Ala Ala Asp Gly Ala Glu Ser Ala Tyr Thr Glu
225                 230                 235                 240

Cys Leu Arg Leu Cys Arg Arg Leu Leu Trp Arg Gln Ser Met Gly Glu
                245                 250                 255

Ser Leu Asp Glu Leu Ser Glu Glu Leu His Arg Ala Trp Gly Gly Gln
                260                 265                 270

Ser Val Asp Phe Leu Pro Gly Glu Leu His Leu Gly Ser Met Arg Arg
                275                 280                 285

Met Leu Glu Ile Leu Ser Arg Gln Ala Leu Pro Leu Asp
        290                 295                 300

<210> SEQ ID NO 13
```

<211> LENGTH: 382
<212> TYPE: PRT
<213> ORGANISM: Pseudomonas aeruginosa

<400> SEQUENCE: 13

```
Met Thr Val Leu Ile Gln Gly Ala Gly Ile Ala Gly Leu Ala Leu Ala
 1               5                  10                  15

Arg Glu Phe Thr Lys Ala Gly Ile Asp Trp Leu Leu Val Glu Arg Ala
            20                  25                  30

Ser Glu Ile Arg Pro Ile Gly Thr Gly Ile Thr Leu Ala Ser Asn Ala
        35                  40                  45

Leu Thr Ala Leu Ser Ser Thr Leu Asp Leu Asp Arg Leu Phe Arg Arg
50                  55                  60

Gly Met Pro Leu Ala Gly Ile Asn Val Tyr Ala His Asp Gly Ser Met
65                  70                  75                  80

Leu Met Ser Met Pro Ser Ser Leu Gly Gly Asn Ser Arg Gly Leu
                85                  90                  95

Ala Leu Gln Arg His Glu Leu His Ala Ala Leu Leu Glu Gly Leu Asp
            100                 105                 110

Glu Ser Arg Ile Arg Val Gly Val Ser Ile Val Gln Ile Leu Asp Gly
        115                 120                 125

Leu Asp His Glu Arg Val Thr Leu Ser Asp Gly Thr Val His Asp Cys
130                 135                 140

Ser Leu Val Val Gly Ala Asp Gly Ile Arg Ser Ser Val Arg Arg Tyr
145                 150                 155                 160

Val Trp Pro Glu Ala Thr Leu Arg His Ser Gly Glu Thr Cys Trp Arg
            165                 170                 175

Leu Val Val Pro His Arg Leu Glu Asp Ala Glu Leu Ala Gly Glu Val
        180                 185                 190

Trp Gly His Gly Lys Arg Leu Gly Phe Ile Gln Ile Ser Pro Arg Glu
    195                 200                 205

Met Tyr Val Tyr Ala Thr Leu Lys Val Arg Arg Glu Glu Pro Glu Asp
210                 215                 220

Glu Glu Gly Phe Val Thr Pro Gln Arg Leu Ala Ala His Tyr Ala Asp
225                 230                 235                 240

Phe Asp Gly Ile Gly Ala Ser Ile Ala Arg Leu Ile Pro Ser Ala Thr
            245                 250                 255

Thr Leu Val His Asn Asp Leu Glu Glu Leu Ala Gly Ala Ser Trp Cys
        260                 265                 270

Arg Gly Arg Val Val Leu Ile Gly Asp Ala Ala His Ala Met Thr Pro
    275                 280                 285

Asn Leu Gly Gln Gly Ala Ala Met Ala Leu Glu Asp Ala Phe Leu Leu
290                 295                 300

Ala Arg Leu Trp Cys Leu Ala Pro Arg Ala Glu Thr Leu Ile Leu Phe
305                 310                 315                 320

Gln Gln Gln Arg Glu Ala Arg Ile Glu Phe Ile Arg Lys Gln Ser Trp
            325                 330                 335

Ile Val Gly Arg Leu Gly Gln Trp Glu Ser Pro Trp Ser Val Trp Leu
        340                 345                 350

Arg Asn Thr Leu Val Arg Leu Val Pro Asn Ala Ser Arg Arg Arg Leu
    355                 360                 365

His Gln Arg Leu Phe Thr Gly Val Gly Glu Met Ala Ala Gln
370                 375                 380
```

<210> SEQ ID NO 14
<211> LENGTH: 398
<212> TYPE: PRT
<213> ORGANISM: Pseudomonas aeruginosa

<400> SEQUENCE: 14

```
Met Thr Asp Asn His Ile Asp Val Leu Ile Asn Gly Cys Gly Ile Gly
 1               5                  10                  15

Gly Ala Met Leu Ala Tyr Leu Leu Gly Arg Gln Gly His Arg Val Val
             20                  25                  30

Val Val Glu Gln Ala Arg Arg Glu Arg Ala Ile Asn Gly Ala Asp Leu
         35                  40                  45

Leu Lys Pro Ala Gly Ile Arg Val Val Glu Ala Ala Gly Leu Leu Ala
     50                  55                  60

Glu Val Thr Arg Arg Gly Gly Arg Val Arg His Glu Leu Glu Val Tyr
 65                  70                  75                  80

His Asp Gly Glu Leu Leu Arg Tyr Phe Asn Tyr Ser Ser Val Asp Ala
                 85                  90                  95

Arg Gly Tyr Phe Ile Leu Met Pro Cys Glu Ser Leu Arg Arg Leu Val
            100                 105                 110

Leu Glu Lys Ile Asp Gly Glu Ala Thr Val Glu Met Leu Phe Glu Thr
        115                 120                 125

Arg Ile Glu Ala Val Gln Arg Asp Glu Arg His Ala Ile Asp Gln Val
    130                 135                 140

Arg Leu Asn Asp Gly Arg Val Leu Arg Pro Arg Val Val Gly Ala
145                 150                 155                 160

Asp Gly Ile Ala Ser Tyr Val Arg Arg Leu Leu Asp Ile Asp Val
                165                 170                 175

Glu Arg Arg Pro Tyr Pro Ser Pro Met Leu Val Gly Thr Phe Ala Leu
            180                 185                 190

Ala Pro Cys Val Ala Glu Arg Asn Arg Leu Tyr Val Asp Ser Gln Gly
        195                 200                 205

Gly Leu Ala Tyr Phe Tyr Pro Ile Gly Phe Asp Arg Ala Arg Leu Val
    210                 215                 220

Val Ser Phe Pro Arg Glu Glu Ala Arg Glu Leu Met Ala Asp Thr Arg
225                 230                 235                 240

Gly Glu Ser Leu Arg Arg Arg Leu Gln Arg Phe Val Gly Asp Glu Ser
                245                 250                 255

Ala Glu Ala Ile Ala Ala Val Thr Gly Thr Ser Arg Phe Lys Gly Ile
            260                 265                 270

Pro Ile Gly Tyr Leu Asn Leu Asp Arg Tyr Trp Ala Asp Asn Val Ala
        275                 280                 285

Met Leu Gly Asp Ala Ile His Asn Val His Pro Ile Thr Gly Gln Gly
    290                 295                 300

Met Asn Leu Ala Ile Glu Asp Ala Ser Ala Leu Ala Asp Ala Leu Asp
305                 310                 315                 320

Leu Ala Leu Arg Asp Ala Cys Ala Leu Glu Asp Ala Leu Ala Gly Tyr
                325                 330                 335

Gln Ala Glu Arg Phe Pro Val Asn Gln Ala Ile Val Ser Tyr Gly His
            340                 345                 350

Ala Leu Ala Thr Ser Leu Glu Asp Arg Gln Arg Phe Ala Gly Val Phe
        355                 360                 365

Asp Thr Ala Leu Gln Gly Ser Ser Arg Thr Pro Glu Ala Leu Gly Gly
    370                 375                 380
```

Glu Arg Ser Tyr Gln Pro Val Arg Ser Pro Ala Pro Leu Gly
385                 390                 395

<210> SEQ ID NO 15
<211> LENGTH: 560
<212> TYPE: DNA
<213> ORGANISM: Pseudomonas aeruginosa

<400> SEQUENCE: 15

| | | | | | |
|---|---|---|---|---|---|
| gtaggtgtcc | tcttcggcag | gctcgcccag | tgtactacgc | aatgggattt | caacagggaa | 60 |
| gcctgcaaat | ggcaggcgag | gcggggcgga | gcgctatcgg | cccgatggat | ggccgcctgc | 120 |
| ttccaggcat | gccgtcgccc | ccttggagcc | caggccgagc | gcctcgaact | gtgagatttg | 180 |
| ggaggcgatt | tgccgagcaa | agtgggttgt | cattggtttg | ccatctcatg | ggttcggacg | 240 |
| aggcctcgag | caagggttgt | aacggttttt | gtctggccaa | tgggctcttg | cgtaaaaagg | 300 |
| ctgccgccct | tcttgcttgg | ttgccgttct | cggatcccgc | gcagcccggt | gggtgtgcca | 360 |
| aatttctcgc | ggtttggatc | gcgccgattg | ccgcggccta | cgaagcccgt | ggttcttctc | 420 |
| cccgaaactt | tttcgttcgg | actccgaata | tcgcgcttcg | cccagcgccg | ctagtttccc | 480 |
| gttcctgaca | aagcaagcgc | tctggctcag | gtatctcctg | atccggatgc | atatcgctga | 540 |
| agagggaacg | ttctgtcatg | | | | | 560 |

<210> SEQ ID NO 16
<211> LENGTH: 999
<212> TYPE: DNA
<213> ORGANISM: Pseudomonas aeruginosa

<400> SEQUENCE: 16

| | | | | | |
|---|---|---|---|---|---|
| atgcctattc | ataacctgaa | tcacgtgaac | atgttcctcc | aggtcatcgc | ctccggttcg | 60 |
| atttcctccg | ctgcgcggat | cctgcgcaag | tcgcacaccg | cggtcagctc | ggcggtcagc | 120 |
| aacctggaaa | tcgacctgtg | cgtggagctg | gtccgtcggg | acggctacaa | ggtcgaaccc | 180 |
| accgagcagg | cgcttcgcct | gatcccttac | atgcgcagcc | tgctgaacta | ccagcagctg | 240 |
| atcggcgaca | tcgccttcaa | tctcaacaag | ggtccgcgca | atctccgggt | gctgctggac | 300 |
| accgccatcc | cgccgtcgtt | ctgcgatacg | gtgagcagcg | tactgctcga | cgatttcaac | 360 |
| atggtcagcc | tgatacgcac | ctcgcccgcc | gatagcctgg | cgacgatcaa | gcaggacaac | 420 |
| gcggaaatcg | atatcgccat | caccatcgac | gaggaactga | agatctcccg | cttcaaccag | 480 |
| tgcgtgctcg | gctacaccaa | ggcgttcgtc | gtcgcccatc | gcagcacccc | gttgtgcaat | 540 |
| gcctccctgc | acagcatcgc | gagcctggcc | aattaccggc | agatcagcct | cggcagccgc | 600 |
| tccgggcagc | attcgaacct | gctgcggccg | gtcagcgaca | aggtgctctt | cgtggaaaac | 660 |
| ttcgacgaca | tgctgcgtct | ggtggaagcc | ggcgtcggat | gggcatcgc | gccgcattat | 720 |
| ttcgtcgagg | aacgcctgcg | caacggtacc | ctggcagtcc | tcagcgaact | ctacgaaccg | 780 |
| ggcggcatcg | acaccaaggt | gtattgctac | tacaacaccg | cgctggaatc | cgagcgcagc | 840 |
| ttcctgcgct | ttctcgaaag | cgcccgccag | cgcctgcgcg | aactcggccg | ccagcgtttc | 900 |
| gacgatgcgc | cggcctggca | accgagcatc | gtcgaaacgg | cgcagcgccg | ctcaggcccg | 960 |
| aaggcgctcg | cgtaccgcca | gcgcgccgca | ccagagtag | | | 999 |

<210> SEQ ID NO 17
<211> LENGTH: 332
<212> TYPE: PRT
<213> ORGANISM: Pseudomonas aeruginosa

```
<400> SEQUENCE: 17

Met Pro Ile His Asn Leu Asn His Val Asn Met Phe Leu Gln Val Ile
1               5                   10                  15

Ala Ser Gly Ser Ile Ser Ser Ala Ala Arg Ile Leu Arg Lys Ser His
                20                  25                  30

Thr Ala Val Ser Ser Ala Val Ser Asn Leu Glu Ile Asp Leu Cys Val
            35                  40                  45

Glu Leu Val Arg Arg Asp Gly Tyr Lys Val Glu Pro Thr Glu Gln Ala
        50                  55                  60

Leu Arg Leu Ile Pro Tyr Met Arg Ser Leu Leu Asn Tyr Gln Gln Leu
65                  70                  75                  80

Ile Gly Asp Ile Ala Phe Asn Leu Asn Lys Gly Pro Arg Asn Leu Arg
                85                  90                  95

Val Leu Leu Asp Thr Ala Ile Pro Pro Ser Phe Cys Asp Thr Val Ser
            100                 105                 110

Ser Val Leu Leu Asp Asp Phe Asn Met Val Ser Leu Ile Arg Thr Ser
        115                 120                 125

Pro Ala Asp Ser Leu Ala Thr Ile Lys Gln Asp Asn Ala Glu Ile Asp
130                 135                 140

Ile Ala Ile Thr Ile Asp Glu Glu Leu Lys Ile Ser Arg Phe Asn Gln
145                 150                 155                 160

Cys Val Leu Gly Tyr Thr Lys Ala Phe Val Val Ala His Pro Gln His
                165                 170                 175

Pro Leu Cys Asn Ala Ser Leu His Ser Ile Ala Ser Leu Ala Asn Tyr
            180                 185                 190

Arg Gln Ile Ser Leu Gly Ser Arg Ser Gly Gln His Ser Asn Leu Leu
        195                 200                 205

Arg Pro Val Ser Asp Lys Val Leu Phe Val Glu Asn Phe Asp Asp Met
210                 215                 220

Leu Arg Leu Val Glu Ala Gly Val Gly Trp Gly Ile Ala Pro His Tyr
225                 230                 235                 240

Phe Val Glu Glu Arg Leu Arg Asn Gly Thr Leu Ala Val Leu Ser Glu
                245                 250                 255

Leu Tyr Glu Pro Gly Gly Ile Asp Thr Lys Val Tyr Cys Tyr Tyr Asn
            260                 265                 270

Thr Ala Leu Glu Ser Glu Arg Ser Phe Leu Arg Phe Leu Glu Ser Ala
        275                 280                 285

Arg Gln Arg Leu Arg Glu Leu Gly Arg Gln Arg Phe Asp Asp Ala Pro
290                 295                 300

Ala Trp Gln Pro Ser Ile Val Glu Thr Ala Gln Arg Arg Ser Gly Pro
305                 310                 315                 320

Lys Ala Leu Ala Tyr Arg Gln Arg Ala Ala Pro Glu
                325                 330
```